United States Patent

Hashimoto et al.

Patent Number: 5,952,299
Date of Patent: Sep. 14, 1999

[54] CYCLIC PEPTIDE NUCLEI AND DERIVATIVES THEREOF

[75] Inventors: Michizane Hashimoto, Tsuchiura; Nobuharu Shigematsu; Seiji Hashimoto, both of Tsukuba, all of Japan

[73] Assignee: Fujisawa Pharmaceutical Co., Ltd., Osaka, Japan

[21] Appl. No.: 08/913,365

[22] PCT Filed: Mar. 26, 1996

[86] PCT No.: PCT/JP96/00774

§ 371 Date: Sep. 29, 1997

§ 102(e) Date: Sep. 29, 1997

[87] PCT Pub. No.: WO96/30399

PCT Pub. Date: Oct. 3, 1996

[30] Foreign Application Priority Data

Mar. 29, 1995 [GB] United Kingdom .................... 9506372

[51] Int. Cl.⁶ .......................... A61K 38/00; A61K 38/12; C07K 5/00; C07K 7/00
[52] U.S. Cl. ................................. 514/9; 514/11; 530/317
[58] Field of Search ................................. 530/317; 514/9, 514/11

*Primary Examiner*—Avis M. Davenport
*Attorney, Agent, or Firm*—Oblon, Spivak, McClelland, Maier & Neustadt, P.C.

[57] ABSTRACT

New peptide compounds of the formula:

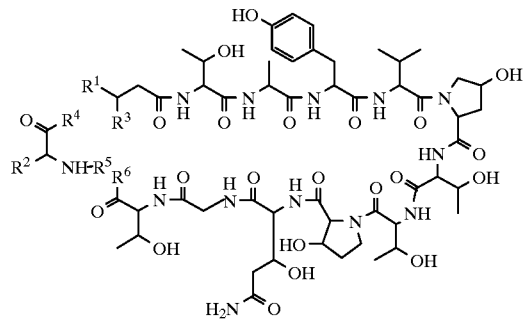

wherein
$R^1$ is alkyl or aralkyl,
$R^2$ is amino(lower)alkyl or protected amino(lower)alkyl,
$R^3$ is hydroxy, protected hydroxy, amino or protected amino,
$R^4$ is hydroxy, or
$R^3$ and $R^4$ are linked together to form —Z— (in which —Z— is —O— or —NH—), and
$R^5$ is hydrogen or an amino protective group,
$R^6$ is hydroxy, or
$R^5$ and $R^6$ are linked together to form bond,
with proviso that
when
$R^3$ is hydroxy, protected hydroxy, amino or protected amino and
$R^4$ is hydroxy,
then $R^5$ and $R^6$ are linked together to form bond,
and a pharmaceutically acceptable salt thereof, which is useful as a medicament.

11 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Xaa Thr Ala Tyr Val Xaa Thr Thr Xaa Xaa Gly Thr Xaa
1             5                   10

(2) INFORMATION FOR SEQ ID NO:2:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Thr Ala Tyr Val Xaa Thr Thr Xaa Xaa Gly Thr
1            5                 10

```
(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Xaa Thr Ala Tyr Val Xaa Thr Thr Xaa Xaa Gly Thr
1               5                   10

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:4:

Xaa Xaa Thr Ala Tyr Val Xaa Thr Thr Xaa Xaa Gly Thr
1               5                   10

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Thr Ala Tyr Val Xaa Thr Thr Xaa Xaa Gly Thr Xaa
1               5                   10

(2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:6:

Lys Xaa Thr Ala Tyr Val Xaa Thr Thr Xaa Xaa Gly Thr
1               5                   10

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Xaa Xaa Thr Ala Tyr Val Xaa Thr Thr Xaa Xaa Gly Thr
1               5                   10
```

(2) INFORMATION FOR SEQ ID NO:8:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Thr Ala Tyr Val Xaa Thr Thr Xaa Xaa Gly Thr Xaa Xaa
1            5                10

CYCLIC PEPTIDE NUCLEI AND DERIVATIVES THEREOF

TECHNICAL FIELD

This invention relates to new peptide compounds and pharmaceutically acceptable salts thereof which are useful as a medicament.

BACKGROUND ART

Some peptide compounds have been known as described, for example, in WO 92/19648.

DISCLOSURE OF INVENTION

This invention relates to new peptide compounds.

One object of this invention is to provide the new and useful peptide compounds and pharmaceutically acceptable salts thereof which possess a high antimicrobial activity (especially, antifungal activity) and a strong inhibitory activity on β-1,3-glucan synthase.

Another object of this invention is to provide process for preparation of the peptide compounds and salts thereof.

A further object of this invention is to provide a pharmaceutical composition comprising, as an active ingredient, said peptide compounds or a pharmaceutically acceptable salt thereof.

Still further object of this invention is to provide a use of said peptide compounds or a pharmaceutically acceptable salt thereof as a medicament for prophylactic and therapeutic treatment of infectious diseases including *Pneumocystis carinii* infection (e.g., *Pneumocystis carinii* pneumonia, etc.) caused by a variety of pathogenic microorganisms in human being and animals.

The object peptide compounds of the present invention are novel and can be represented by the following general formula (I) (SEQ ID NO:1):

wherein $R^1$ is alkyl or aralkyl, $R^2$ is amino(lower)alkyl or protected amino(lower)alkyl, $R^3$ is hydroxy, protected hydroxy, amino or protected amino, $R^4$ is hydroxy, or $R^3$ and $R^4$ are linked together to form —Z— (in which —Z— is —O— or —NH—), and $R^5$ is hydrogen or an amino protective group, $R^6$ is hydroxy, or $R^5$ and $R^6$ are linked together to form bond, with proviso that when $R^3$ is hydroxy, protected hydroxy, amino or protected amino and $R^4$ is hydroxy, then $R^5$ and $R^6$ are linked together to form bond.

The object compound (I) of the present invention can be prepared by the processes as illustrated in the following.

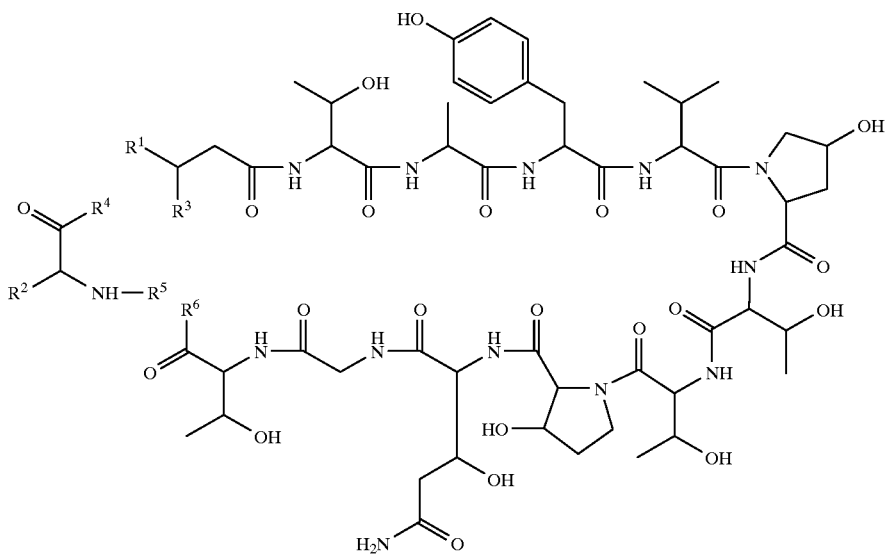

Process (1)
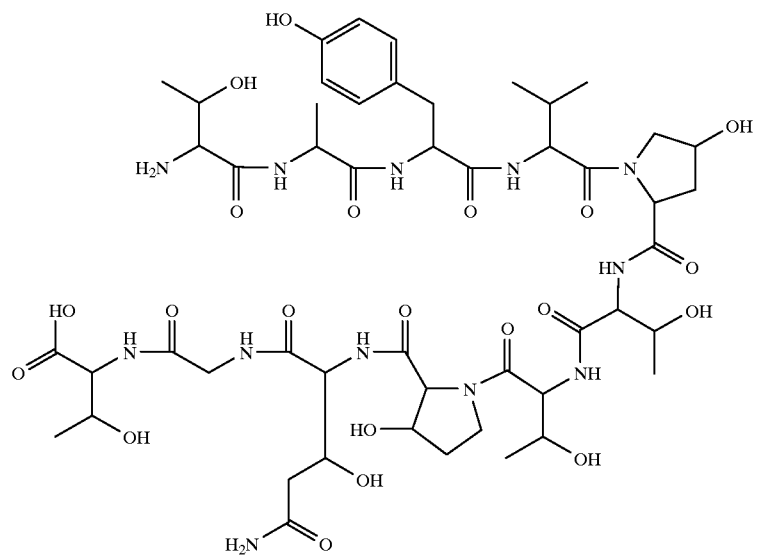
(II) (SEQ ID NO: 2)
or its reactive derivative at the amino group,
or a salt thereof
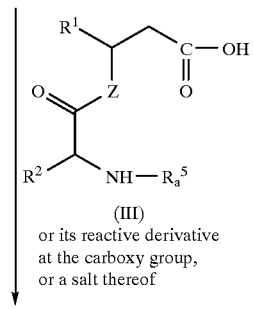
(III)
or its reactive derivative
at the carboxy group,
or a salt thereof
elimination reaction of the
amino protective group -continued
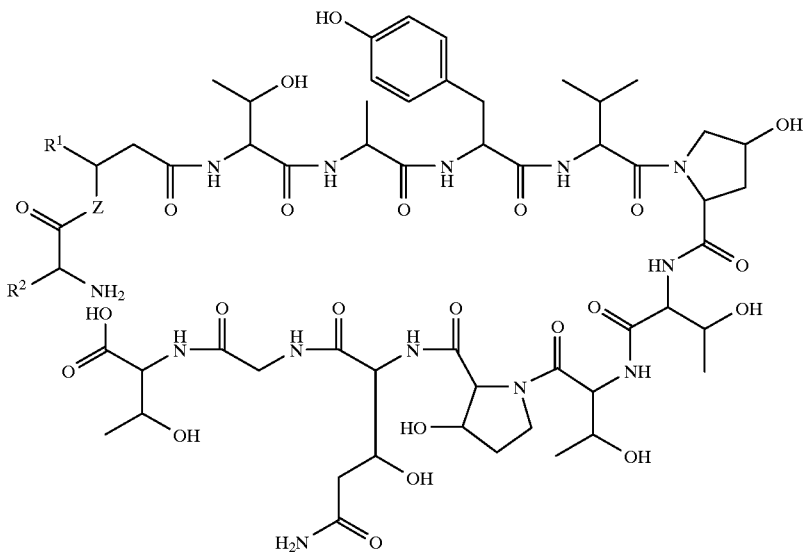
(Ic) (SEQ ID NO: 3)
or a salt thereof
Process (3)
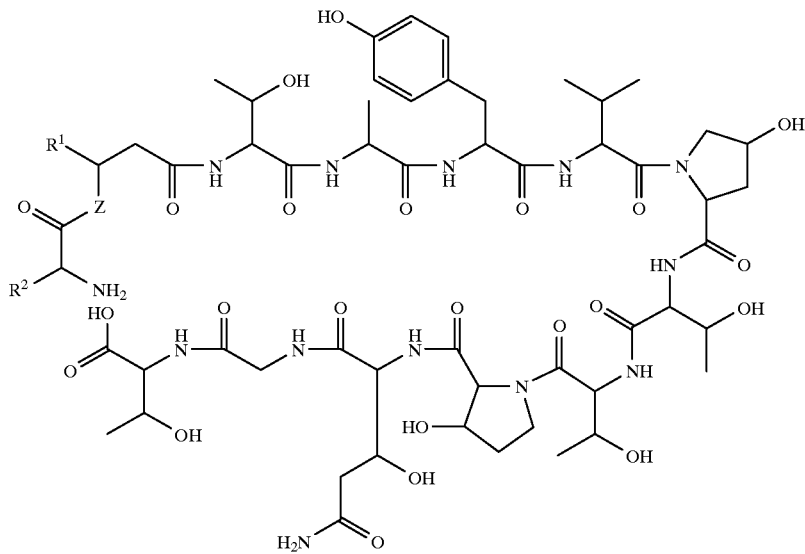
(Ic) (SEQ ID NO: 3)
or a salt thereof
cyclization

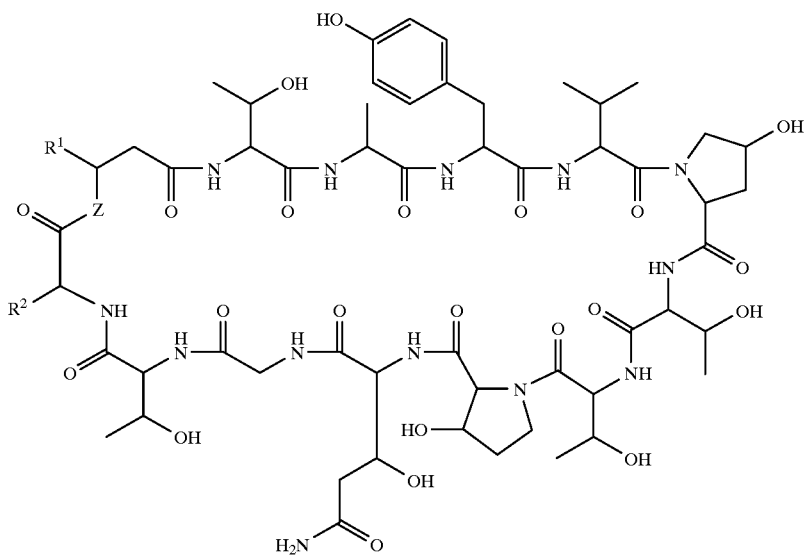
(Id) (SEQ ID NO: 3)
or a salt thereof
Process (4)
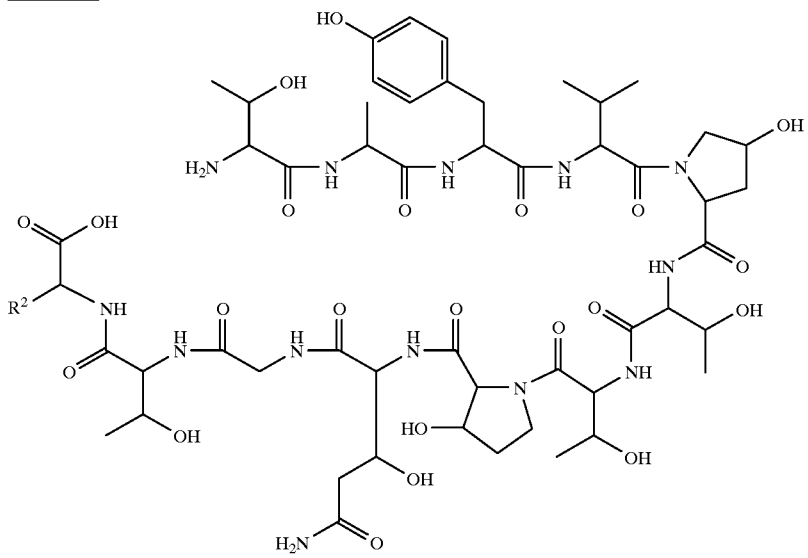
(IV) (SEQ ID NO: 5)
or its reactive derivative at the amino group,
or a salt thereof
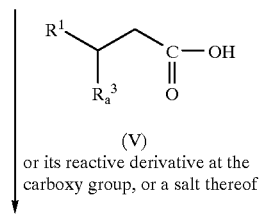
(V)
or its reactive derivative at the
carboxy group, or a salt thereof -continued
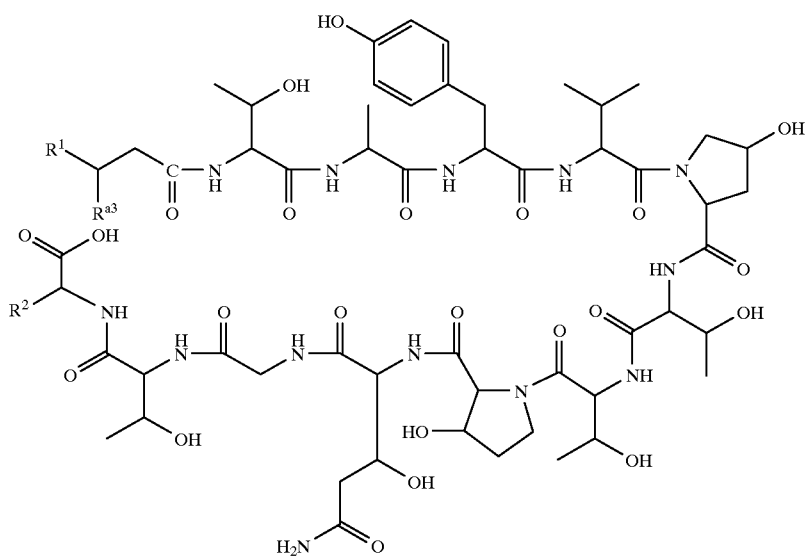
(Ie) (SEQ ID NO: 1)
or a salt thereof
Process (5)
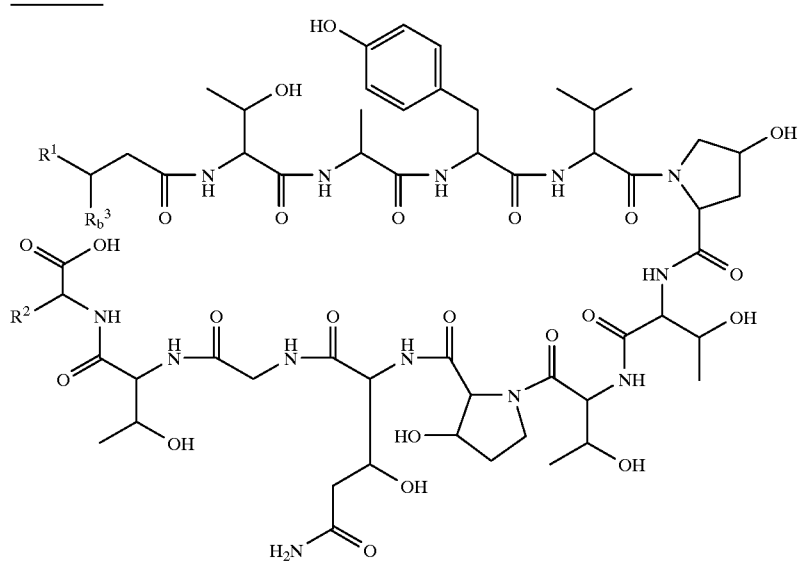
(If) (SEQ ID NO: 1)
or a salt thereof
| elimination reaction of the amino protective group
▼

-continued
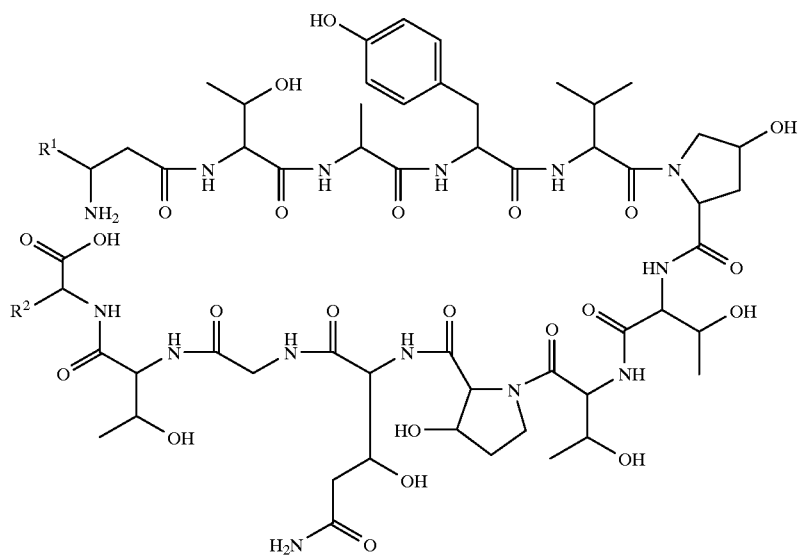
(Ig) (SEQ ID NO: 1)
or a salt thereof
Process (6)
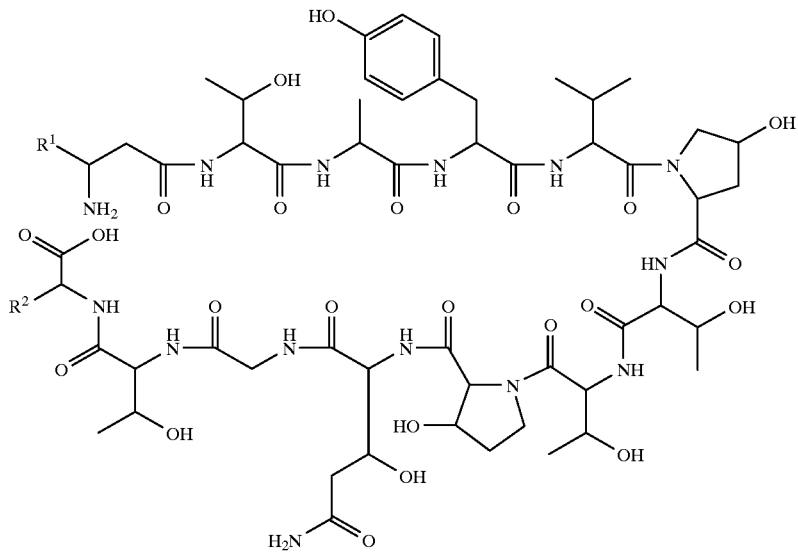
(Ig) (SEQ ID NO: 1)
or a salt thereof
↓ cyclization -continued
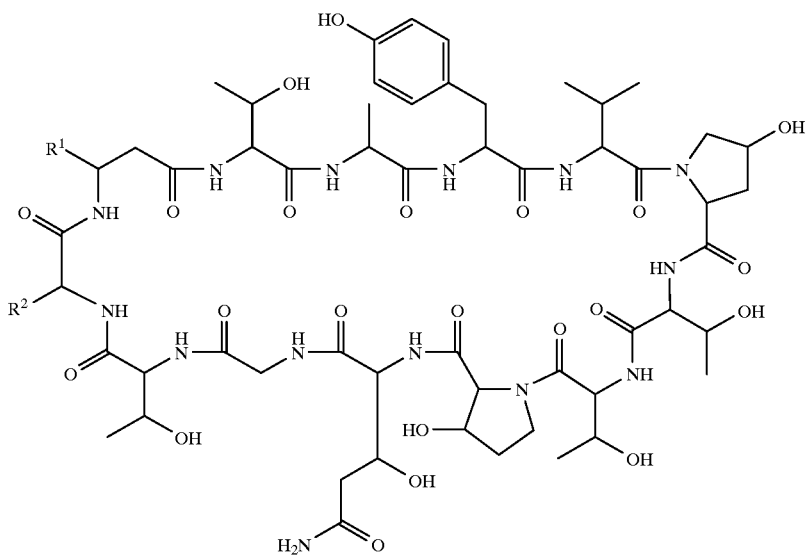
(Ih) (SEQ ID NO: 4)
or a salt thereof
Process (7)
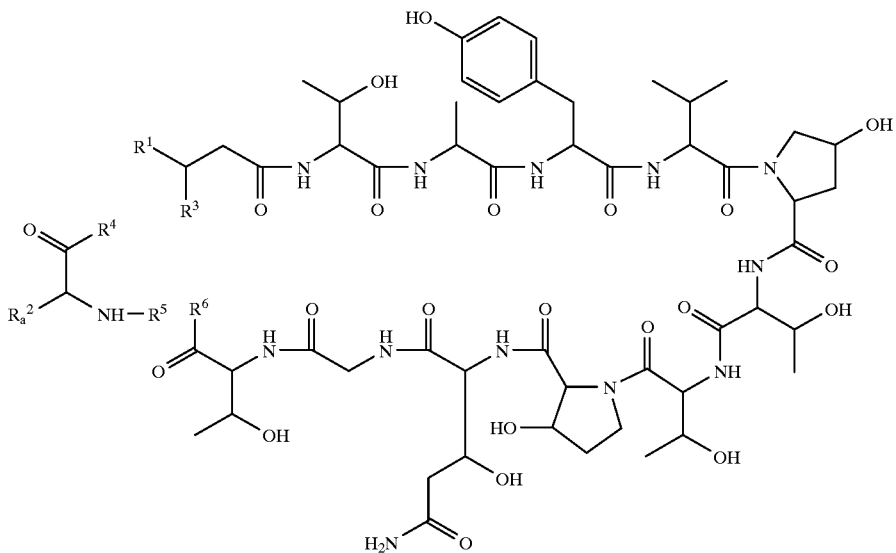
(Ii) (SEQ ID NO: 1)
or its reactive derivative at the amino group,
or a salt thereof
↓ acylation -continued
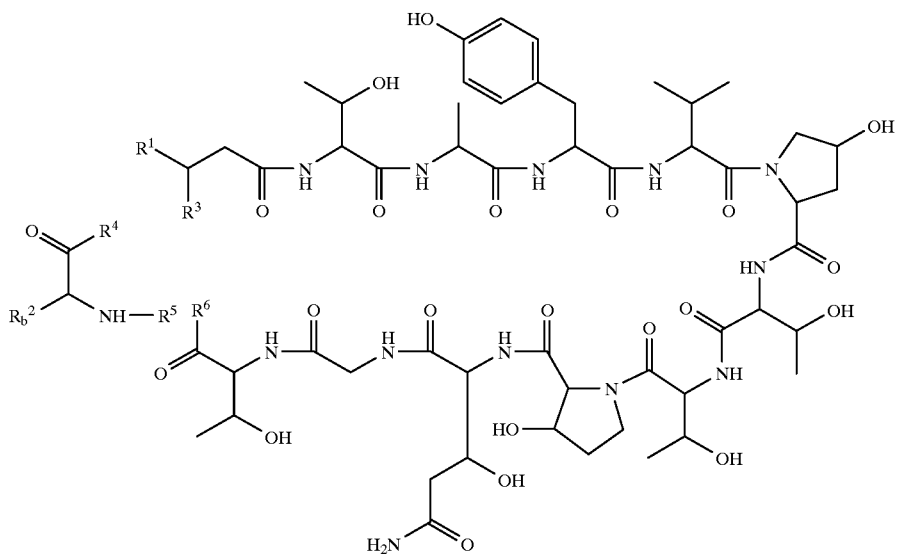
(Ij) (SEQ ID NO: 1)
or a salt thereof
Process (8)
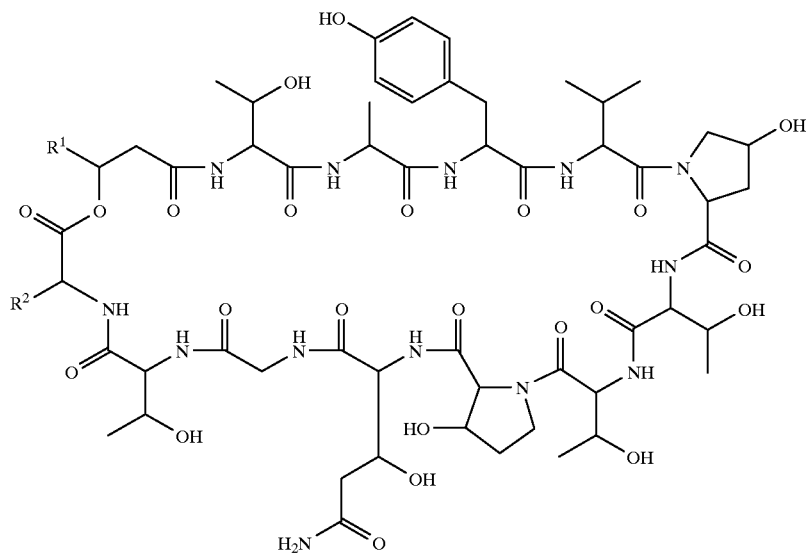
(Ik) (SEQ ID NO: 4)
or a salt thereof
↓ Hydrolysis -continued

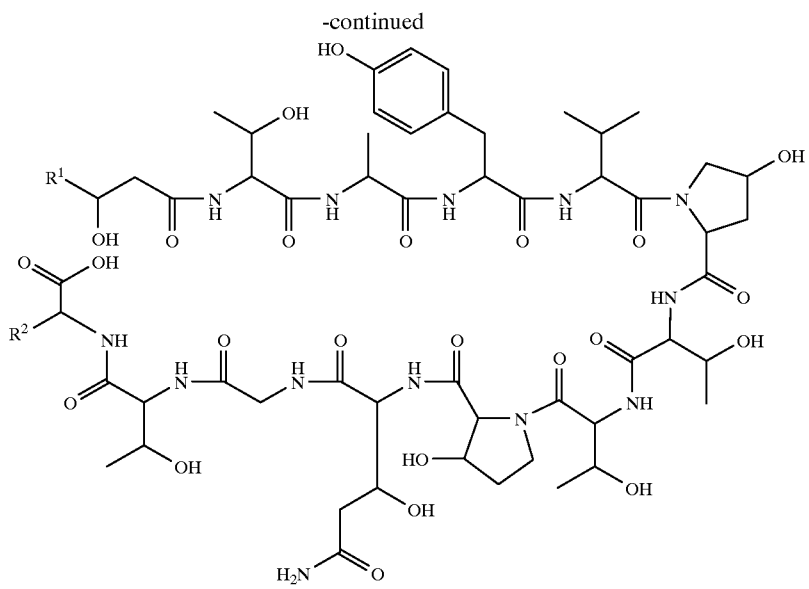

(II) (SEQ ID NO: 1)
or a salt thereof wherein $R^1$, $R^2$, $R^3$, $R^4$, $R^5$, $R^6$ and —Z— are each as defined above, $R_a^2$ is amino(lower)alkyl, $R_b^2$ is acylamino(lower)alkyl, $R_a^3$ is amino or protected amino, $R_b^3$ is protected amino, $R_a^5$ is hydrogen or an amino protective group, and $R_b^5$ is an amino protective group.

The starting compounds (II) and (IV) of the present invention can be prepared by the processes as illustrated in the following.

Process (A)

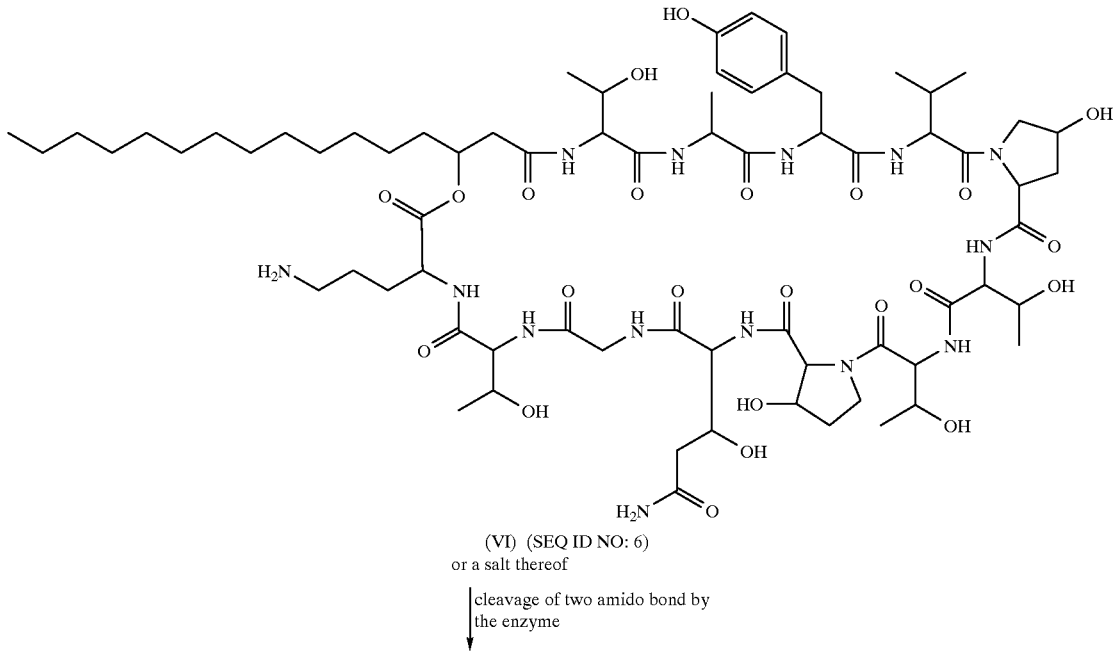

(VI) (SEQ ID NO: 6)
or a salt thereof cleavage of two amido bond by the enzyme

-continued
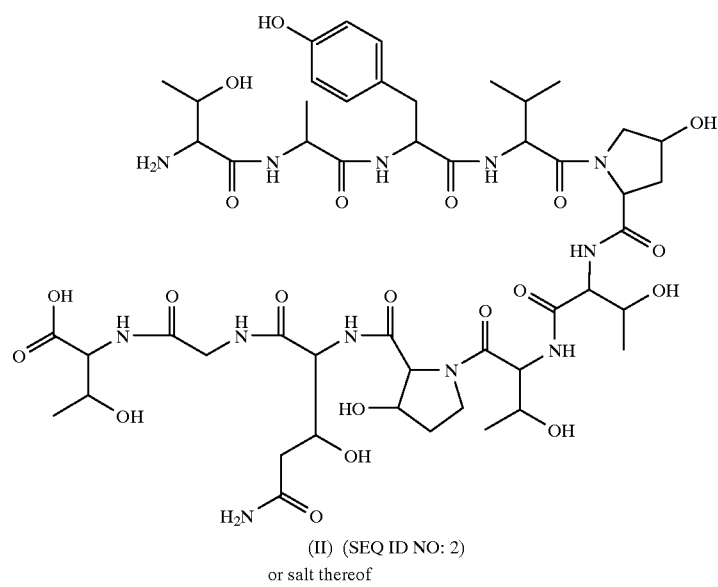
(II) (SEQ ID NO: 2)
or salt thereof
Process (B)
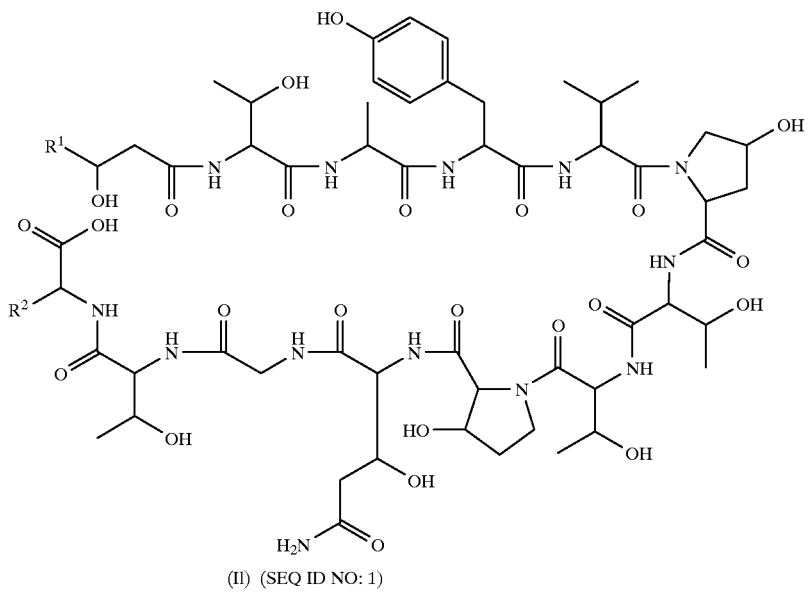
(II) (SEQ ID NO: 1)
or a salt thereof
↓ deacylation -continued

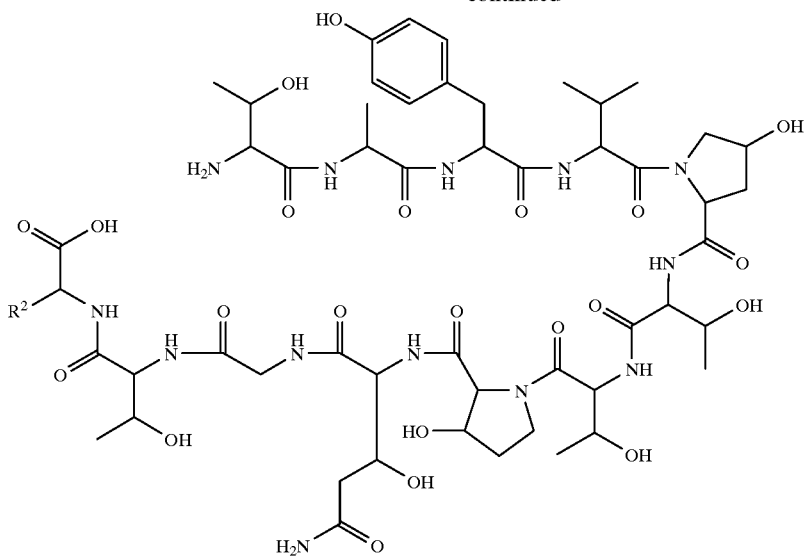

(IV) (SEQ ID NO: 5)
or a salt thereof wherein $R^1$ and $R^2$ are each as defined above.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

The term "higher" is used to intend a group having 7 to 20 carbon atoms, unless otherwise provided.

Suitable "lower alkyl" and "lower alkyl moiety" in the terms "amino(lower)alkyl", "acylamino(lower)alkyl" and "protected amino(lower)alkyl" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like.

Suitable "alkyl" and "alkyl moiety" in the term "aralkyl" may include straight or branched one having 1 to 20 carbon atom(s), such as methyl, ethyl, propyl, isopropyl, butyl, isobutyl, sec-butyl, tert-butyl, pentyl, tert-pentyl, hexyl, heptyl, octyl, nonyl, decyl, undecyl, dodecyl, tridecyl, tetradecyl, pentadecyl, and the like.

Suitable "aryl moiety" in the term "aralkyl" may include phenyl, naphthyl and the like.

Suitable "hydroxy protective group" in the term "protected hydroxy" may include acyl, mono(or di or tri)phenyl (lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

Suitable "amino protective group" may include acyl, and the like.

Suitable "protected amino" and "protected amino moiety" in the term "protected amino(lower)alkyl" may include acylamino or an amino group substituted by a conventional protecting group such as mono (or di or tri)aryl(lower)alkyl, for example, mono(or di or tri)phenyl(lower)alkyl (e.g., benzyl, trityl, etc.) or the like.

Suitable "acyl" and "acyl moiety" in the terms "acylamino", "acylamino(lower)alkyl" and "acyloxy" may include carbamoyl, aliphatic acyl group and acyl group containing an aromatic ring, which is referred to as aromatic acyl.

Suitable example of said acyl may be illustrated as follows:

Carbamoyl; Thiocarbamoyl;

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.); lower or higher alkylsulfonyl (e.g., methylsulfonyl, ethylsulfonyl, etc.);

lower or higher alkoxysulfonyl (e.g., methoxysulfonyl, ethoxysulfonyl, etc.); cyclo(lower)alkylcarbonyl (e.g., cyclopentylcarbonyl, cyclohexylcarbonyl, etc.); or the like;

Aromatic acyl such as aroyl (e.g., benzoyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower)alkenoyl (e.g., naphthylpropenoyl, naphthylbutenoyl, etc.), etc.];

ar(lower)alkoxycarbonyl [e.g., phenyl(lower)alkoxycarbonyl (e.g., benzyloxycarbonyl, etc.), etc.];

aryloxycarbonyl (e.g., phenoxycarbonyl, naphthyloxycarbonyl, etc.); aryloxy(lower)alkanoyl (e.g., phenoxyacetyl, phenoxypropionyl, etc.); arylglyoxyloyl (e.g., phenylglyoxyloyl, naphthylglyoxyloyl, etc.);

arylsulfonyl (e.g., phenylsulfonyl, p-tolylsulfonyl, etc.); or the like; and the like.

Preferred embodiments of the object compound (I) are as follows.

wherein $R^1$ is $C_1$–$C_{13}$ alkyl or phenyl($C_1$–$C_6$)alkyl, $R^2$ is amino(lower)alkyl or acylamino(lower)alkyl (more preferably lower alkoxycarbonylamino(lower)alkyl, $R^3$ is hydroxy, acyloxy, amino or acylamino (more preferably ar(lower)alkoxycarbonylamino; most preferably phenyl(lower)alkoxycarbonylamino), $R^4$ is hydroxy, or $R^3$ and $R^4$ are linked together to form —Z— (in which —Z— is —O— or —NH—), and $R^5$ is hydrogen or acyl (more preferably ar(lower)alkoxycarbonyl; most preferably phenyl(lower)alkoxycarbonyl, $R^6$ is hydroxy, or $R^5$ and $R^6$ are linked together to form bond, with proviso that when $R^3$ is hydroxy, acyloxy, amino or acylamino (more preferably are(lower)alkoxycarbonyl; most preferably phenyl(lower)alkoxycarbonyl) and $R^4$ is hydroxy, then $R^5$ and $R^6$ are linked together to form bond.

The processes for preparing the object and the starting compounds are explained in detail in the following.

PROCESS (1)

The compound (Ia) or a salt thereof can be prepared by reacting the compound (II) or its reactive derivative at the amino group, or a salt thereof with the compound (III) or its reactive derivative at the carboxy group, or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as N,O-bis(trimethylsilyl)acetamide, N-trimethylsilylacetamide or the like; a derivative formed by the reaction of the compound (II) with phosphorus trichloride or phosgene, and the like.

Suitable reactive derivative of the compound (III) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid, (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl [$(CH_3)_2^+$N=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them accordingly to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction, or the mixture thereof.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole; pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine (e.g., triethylamine, etc.), pyridine, N-(lower)alkylmorphorine, N,N-di(lower) alkylbenzylamine, or the like.

The reaction temperature is not critical, and the reaction is usually carried out under cooling to heating.

PROCESS (2)

The compound (Ic) or a salt thereof can be prepared by subjecting the compound (Ib) or a salt thereof to elimination reaction of the amino protective group.

Suitable method of this elimination reaction may include conventional one such as hydrolysis, reduction and the like.

(i) For hydrolysis:

the hydrolysis is preferably carried out in the presence of a base or an acid including Lewis acid.

Suitable base may include an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]-non-5-ene, or the like.

Suitable acid may include an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], or the like is preferably carried out in the presence of cation trapping agents [e.g., anisole, phenol, etc.].

The reaction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or the mixture thereof.

The reaction temperature is not critical and the reaction is usually carried out under cooling to warming.

(ii) For reduction:

Reduction is carried out in a conventional manner, including chemical reduction and catalytic reduction, Suitable reducing reagent to be used in chemical reduction are hydrides (e.g., hydrogen iodide, hydrogen sulfide, lithium aluminum hydride, sodium borohydride, sodium cyanoborohydride, etc.), or a combination of a metal (e.g., tin, zinc, iron, etc.) or metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, Ullman iron, etc.), and the like.

The reduction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or the mixture thereof.

Additionally, in case that the above-mentioned acids to be used in chemical reduction are in liquid, they can also be used as a solvent.

The reaction temperature of this reduction is not critical and the reaction is usually carried out under cooling to warming.

PROCESS (3)

The compound (Id) or a salt thereof can be prepared by subjecting the compound (Ic) or a salt thereof to cyclization reaction.

The reaction is usually carried out in a conventional solvent such as acetonitrile, chloroform, methylene chloride, ethylene chloride, tetrahydrofuran, N,N-dimethylformamide or any other organic solvents which do not adversely affect the reaction, or the mixture thereof.

The reaction is usually carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzensulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine, pyridine, N-(lower) alkylmorphorine, N,N-di(lower)alkylbenzylamine, or the like.

The reaction temperature is not critical, and the reaction is usually carried out under cooling to heating.

The reaction is preferably carried out in the presence of a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.).

PROCESS (4)

The compound (Ie) or a salt thereof can be prepared by reacting the compound (IV) or its reactive derivative at the amino group, or a salt thereof with the compound (V) or its reactive derivative at the carboxy group, or a salt thereof.

This reaction can be carried out in a similar manner to that of the aforementioned Process (1), and therefore the reagents to be used and the reaction conditions (e.g., solvent, reaction temperature, etc.) can be referred to those of the Process (1).

PROCESS (5)

The compound (Ig) or a salt thereof can be prepared by subjecting the compound (If) or a salt thereof to elimination reaction of the amino protective group.

This reaction can be carried out in a similar manner to that of the aforementioned Process (2), and therefore the reagents to be used and the reaction conditions (e.g., solvent, reaction temperature, etc.) can be referred to those of the Process (2).

PROCESS (6)

The compound (Ih) or a salt thereof can be prepared by subjecting the compound (Ig) or a salt thereof to cyclization reaction.

This reaction can be carried out in a similar manner to that of the aforementioned Process (3), and therefore the reagents to be used and the reaction conditions (e.g., solvent, reaction temperature, etc.) can be referred to those of the Process (3).

PROCESS (7)

The compound (Ij) or a salt thereof can be prepared by subjecting the compound (Ii) or its reactive derivative at the amino group, or a salt thereof to acylation reaction.

Suitable acylating agent to be used in the present acylation reaction may include the compound of the formula:

$$R^7\text{—OH} \tag{VII}$$

(wherein $R^7$ is acyl) or its reactive derivative, or a salt thereof.

Suitable reactive derivative at the amino group of the compound (Ii) may include Schiff's base type imino or its tautomeric enamine type isomer formed by the reaction of the compound (Ii) with a carbonyl compound such as aldehyde, ketone or the like; a silyl derivative formed by the reaction of the compound (Ii) with a silyl compound such as N,O-bis(trimethylsilyl)acetamide, N-trimethylsilylacetamide or the like; a derivative formed by the reaction of the compound (Ii) with phosphorus trichloride or phosgene, and the like.

Suitable reactive derivative of the compound (VII) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfuric acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl [$(CH_3)_2^+$ N=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them accordingly to the kind of the compound (VII) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction, or the mixture thereof.

When the compound (VII) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine, pyridine, N-(lower) alkylmorphorine, N,N-di(lower)alkylbenzylamine, or the like.

The reaction temperature is not critical, and the reaction is usually carried out under cooling to heating.

PROCESS (8)

The compound (II) or a salt thereof can be prepared by subjecting the compound (Ik) or a salt thereof to hydrolysis reaction.

This reaction can be carried out in a similar manner to that of the aforementioned Process (2), and therefore the reagents to be used and the reaction conditions (e.g., solvent, reaction temperature, etc.) can be referred to those of the Process (2).

PROCESS (A)

The compound (II) or a salt thereof can be prepared by subjecting the compound (VI) or a salt thereof to cleavage reaction of two amido bond by the enzyme.

Suitable example of said enzyme may include the one produced by certain microorganisms of the Acetinoplanaceae, for example, Actinoplanes utahensis IFO-13244, Actinoplanes utahensis ATCC 12301, Actinoplanes missourienses NRRL 12053, or the like; and the like.

This reaction is usually carried out in a solvent such as phosphate buffer, Tris-HCl buffer or any other solvent which does not adversely affect the reaction.

The reaction temperature is not critical and the reaction can be carried out at room temperature or under warming.

PROCESS (B)

The compound (IV) or a salt thereof can be prepared by subjecting the compound (II) or a salt thereof to deacylation.

This reaction is carried out in accordance with a conventional method such as hydrolysis, reduction, reaction with an enzyme or the like.

The said hydrolysis and reduction can be carried out in a similar manner to that of the aforementioned Process (2), and therefore the reagents to be used and the reaction conditions (e.g., solvent, reaction temperature, etc.) can be referred to those of the Process (2).

Further, the said reaction with the enzyme can be carried out in a similar manner to that of the aforementioned Process (A), and therefore the reagents to be used and the reaction conditions (e.g., solvent, reaction temperature, etc.) can be referred to those of the Process (A).

The object and starting compounds, and pharmaceutically acceptable salts thereof may include a solvate [e.g., enclosure compound (e.g. hydrate, etc.)].

Suitable salts of the object, starting compounds and their reactive derivatives in Processes (1)~(8), (A) and (B) can be referred to the ones as exemplified for the compound (I).

The compounds obtained by the above processes can be isolated and purified by a conventional method such as pulverization, recrystallization, column chromatography, reprecipitation, or the like.

It is to be noted that the compound (I) and the other compounds may include one or more steroisomer(s) such as optical isomer(s) and geometrical isomer(s) due to asymmetric carbon atom(s) and double bond(s), and all of such isomers and mixture thereof are included within the scope of this invention.

The object compounds (I) and pharmaceutically acceptable salts thereof possess a high antimicrobial activity (especially, antifungal activity) inhibiting the growth of a variety of pathogenic microorganisms, and a strong inhibitory activity on β-1,3-glucan synthase.

Accordingly, they are useful for prevention and/or treatment of infectious diseases including *Pneumocystis carinii* infection (e.g. *Pneumocystis carinii* pneumonia) caused by a variety of pathogenic microorganisms.

The pharmaceutical composition of this invention can be used in the form of a pharmaceutical preparation, for example, in solid, semisolid or liquid form, which contains the peptide compound (I) or a pharmaceutically acceptable salt thereof, as an active ingredient in admixture with an organic or inorganic carrier, or excipient suitable for rectal, pulmonary (nasal or buccal inhalation), nasal, ocular, external (topical), oral, or parenteral (including subcutaneous, intravenous and intramuscular) administration or insufflation. The active ingredient may be compound, for example, with the usual non-toxic, pharmaceutically acceptable carrier for tablets, petters, torches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used. The peptide compound (I) or a pharmaceutically acceptable salt thereof is/are included in the pharmaceutical composition in an amount sufficient to produce the desired antimicrobial effect upon the process or condition of diseases. For applying the composition to human, it is preferable to apply it by intravenous, intramuscular, pulmonary, or oral administration, or insufflation. While the dosage of therapeutically effective amount of the peptide compound (I) varies from and also depends upon the age and condition of each individual patient to be treated, in the case of intravenous administration, a daily dose of 0.01–20 mg of the peptide compound (I) per kg weight of human being in the case of intramuscular administration, a daily dose of 0.1–20 mg of the peptide compound (I) per kg weight of human being, in case of oral administration, a daily dose of 0.5–50 mg of the peptide compound (I) per kg weight of human being is generally given for treating or preventing infectious diseases.

Especially in case of the treatment or prevention of *Pneumocystis carinii* infection, the followings are to be noted.

For administration of inhalation, the compounds of the present invention are conveniently delivered in the form of an aerosol spray presentation from pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol administration is a preferred method of administration. Insufflation is also a desirable method, especially where infection may have spread to ears and other body cavities.

Alternatively, parenteral administration may be employed using drip intravenous administration.

The following Preparations and Examples are given for the purpose of illustrating the present invention in more detail

PREPARATION 1

To a solution of methyl (3R)-3-hydroxy hexadecanoate (2.0 g) in methanol (30 ml) was added a 1N aqueous sodium hydroxide (10 ml). Reaction mixture was refluxed at 80° C. for 30 minutes. After the solvent was evaporated, the residue was dissolved in ethyl acetate and washed with 1N hydrochloric acid. The organic layer was dried over with sodium sulfate and evaporated in vacuo to give (3R)-3-hydroxy hexadecanoic acid (1.95 g).

To a solution of (3R)-3-hydroxy hexadecanoic acid (1.95 g) in dichloromethane (20 ml) was added 2,2,2-trichloroethanol (688 ul), 1-ethyl-3-(3-dimethylaminopropyl)carbodiimide hydrochloride (1.37 g) and 4-dimethylamino pyridine (87.6 mg) and the reaction mixture was stirred for 1 hour at room temperature. After the solvent was evaporated, the residue was dissolved in ethyl acetate and washed with 1N hydrochloric acid, a saturated aqueous sodium bicarbonate and water successively. After drying over with magnesium sulfate, solvent was evaporated to give 2,2,2-trichloroethyl (3R)-3-hydroxy hexadecanoate (2.95 g).

To a solution of $N^2$-benzyloxycarbonyl-$N^5$-tert-butoxycarbonyl-L-ornithine (73.3 mg) and 2,2,2-trichloroethyl (3R)-3-hydroxy hexadecanoate (80.7 mg) in dichloromethane (2 ml) was added (benzotriazol-1-yl)oxy-tripyrrolidinophosphonium hexafluorophosphate(PyBop) (104.1 mg) and 4-dimethylamino pyridine (48.8 mg) at room temperature. After the solution was stirred for 6.5 hours, solvent was evaporated in vacuo. The residue was purified by preparative thin layer chromatography (merck 5744 (Merck Co., Ltd.)) to give 2,2,2-trichloroethyl (3R)-3-[$N^2$-benzyloxycarbonyl-$N^5$-tert-butoxycarbonyl-L-ornithyl]oxy-hexadecanoate (50 mg).

$^1$H NMR (300 MHz, $CDCl_3$, δ): 7.36 (5H, m), 5.35 (1H, m), 5.30 (1H, m), 5.10 (2H, s), 4.75 (2H, s), 4.58 (1H, m), 4.34 (1H, m), 3.12 (2H, m), 2.74 (2H, m), 1.95–1.20 (28H, m), 1.43 (9H, s), 0.88 (3H, t, J=7 Hz)

FABMS (m/z): 751 (M+H)$^+$

PREPARATION 2

To a solution of $N^2$-benzyloxycarbonyl-$N^6$-tert-butoxycarbonyl-L-lysine (76.1 mg) and 2,2,2-trichloroethyl (3R)-3-hydroxy hexadecanoate (80.7 mg) in dichloromethane (0.5 ml) was added (benzotriazol-1-yl)oxy-tripyrrolidinophosphonium hexafluorophosphate (PyBop) (104.1 mg) and 4-dimethylamino pyridine (48.8 mg) at room temperature. After the solution was stirred for 6.5 hours, the solvent was evaporated in vacuo. The residue was purified by preparative thin layer chromatography (merck 5744) to give 2,2,2-trichloroethyl (3R)-3-[$N^2$-benzyloxycarbonyl-$N^6$-tert-butoxycarbonyl-L-lysyl]oxy-hexadecanoate (79.4 mg).

$^1$H NMR (300 MHz, $CDCl_3$, δ): 7.34 (5H, m), 5.38 (1H, m), 5.30 (1H, m), 5.09 (2H, s), 4.74 (2H, s), 4.59 (1H, m), 4.31 (1H, m), 3.09 (2H, m), 2.74 (2H, m), 1.83 (2H, m), 1.65 (4H, m), 1.42 (9H, s), 1.55–1.20 (24H, m), 0.86 (3H, t, J=6 Hz)

FABMS (m/z): 787 (M+Na)$^+$

PREPARATION 3

To a solution of 2,2,2-trichloroethyl (3R)-3-[$N^2$-benzyloxycarbonyl-$N^5$-tert-butoxycarbonyl-L-ornithyl]oxy-hexadecanoate (100 mg) in 90% aqueous acetic acid (3 ml) was added zinc powder (400 mg) at 0° C. and stirred for 1 hour. After the reaction mixture was filtered, the filtrate was evaporated in vacuo. The residue was dissolved in ethyl acetate and washed with diluted hydrochloric acid. The organic layer was dried over with sodium sulfate and evaporated in vacuo to give (3R)-3-[$N^2$-benzyloxycarbonyl-$N^5$-tert-butoxycarbonyl-L-ornithyl]oxy-hexadecanoic acid (86.5 mg).

$^1$H NMR (300 MHz, CDCl$_3$, δ): 7.34 (5H, m), 5.45 (1H, d, J=8 Hz), 5.30 (1H, m), 5.10 (2H, s), 4.80 (1H, m), 4.30 (1H, m), 3.08 (2H, m), 2.59 (2H, m), 1.80–1.20 (28H, m), 1.43 (9H, s), 0.87 (3H, t, J=7 Hz)

FABMS (m/z): 643 (M+Na)$^+$

PREPARATION 4

The following compound was obtained according to a similar manner to that of Preparation 3.

(3R)-3-[$N^2$-Benzyloxycarbonyl-$N^6$-tert-butoxycarbonyl-L-lysyl]oxy-hexadecanoic acid.

$^1$H NMR (300 MHz, CDCl$_3$, δ): 7.35 (5H, m), 6.32 (1H, m), 5.35 (2H, m), 5.11 (2H, s), 4.76 (1H, m), 4.38 (1H, m), 3.10 (2H, m), 2.58 (2H, m), 1.85–1.20 (39H, m), 0.88 (3H, t, J=6 Hz)

FABMS (m/z): 657 (M+Na)$^+$

IR (KBr): 3355, 2925, 1730, 1725, 1685, 1650, 1525 cm$^{-1}$ $[α]_D^{22}$=+4.0° (C=1.0, CHCl$_3$)

The Starting Compounds used and the Object Compounds obtained in the following Preparations and Examples are given in the Table as below, in which the formulae of the Starting Compounds are in the upper and the formulae of the Object Compounds are in the lower, respectively, unless otherwise provided.

In the following Examples and Preparations, there are employed the other abbreviations in addition to the abbreviations adopted by the IUPAC-IUB (Commission on Biological Nomenclature).

The abbreviations used are as follows.

Boc: t-butoxycarbonyl.
Z: benzyloxycarbonyl

TABLE

| Preparation No. | |
| --- | --- |
| 5 | Upper sequence: SEQ ID NO: 6, Lower Sequence: SEQ ID NO: 2. |

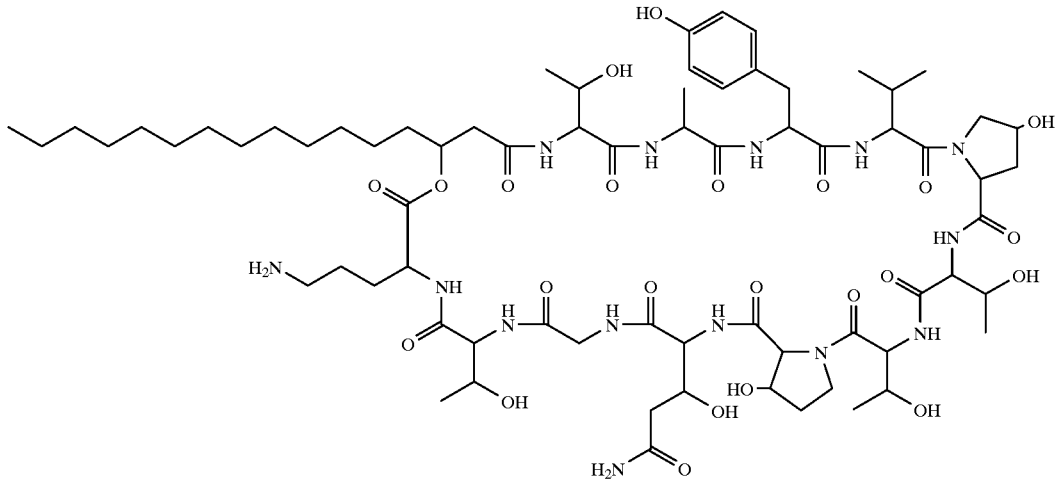

TABLE-continued
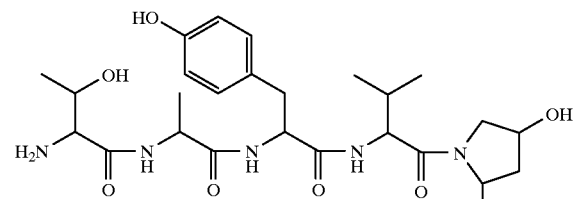
6      Upper Sequence: SEQ ID NO: 4, Lower sequence: SEQ ID NO 1.
Starting Compound
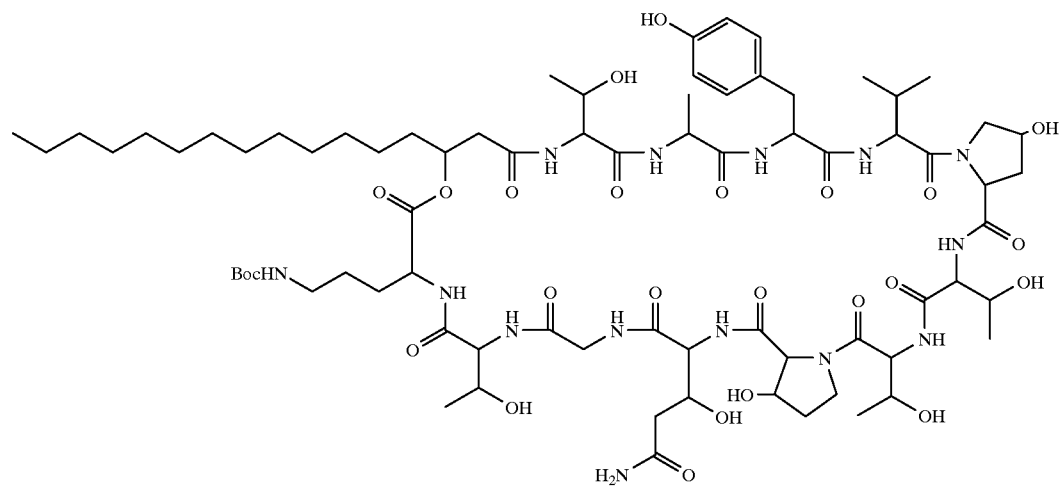
Compound A
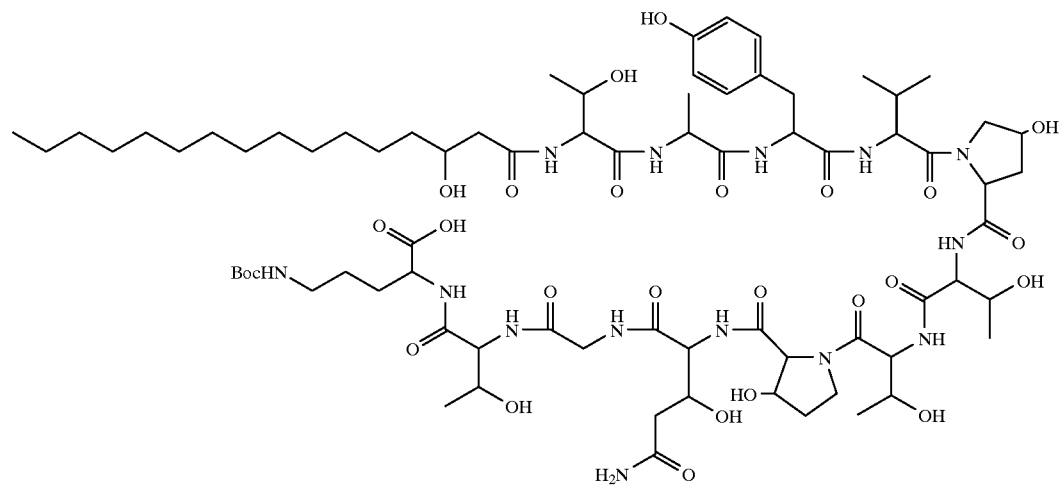

TABLE-continued
SEQ ID NO: 5
Object Compound
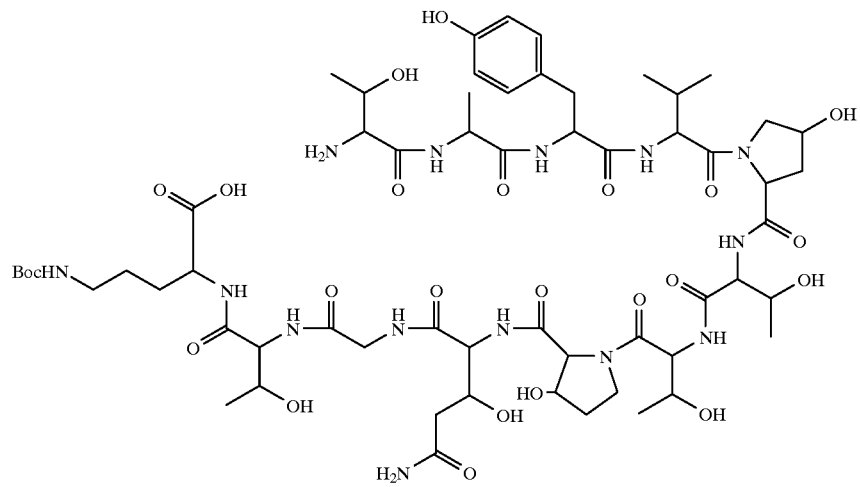
| Example No. | |
|---|---|
| 1 | Upper Sequence: SEQ ID NO: 2, Lower sequence: SEQ ID NO: 7. |
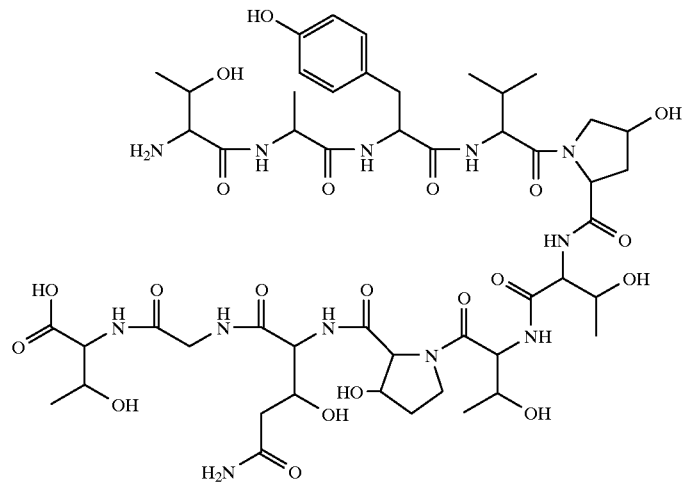

TABLE-continued
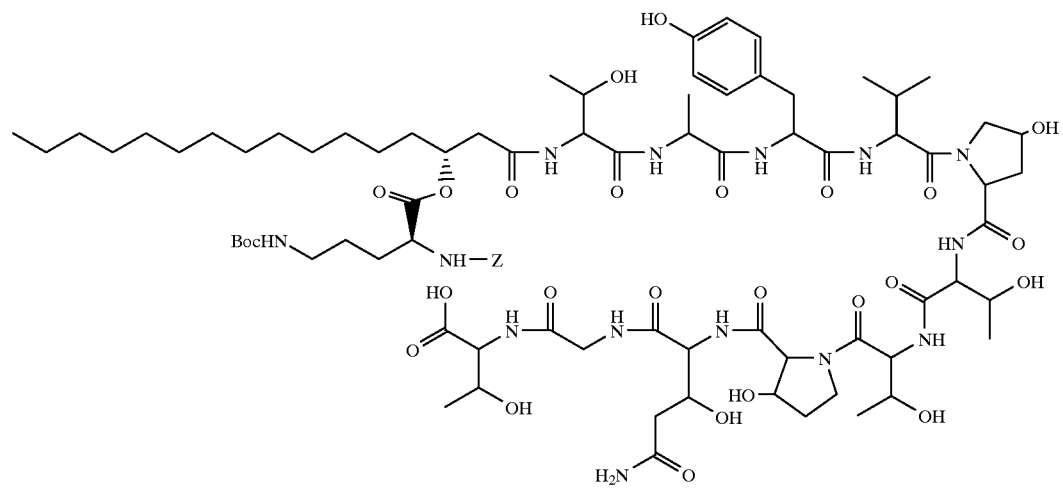
2  Upper sequence: SEQ ID NO: 5, Lower sequence: SEQ ID NO: 7.
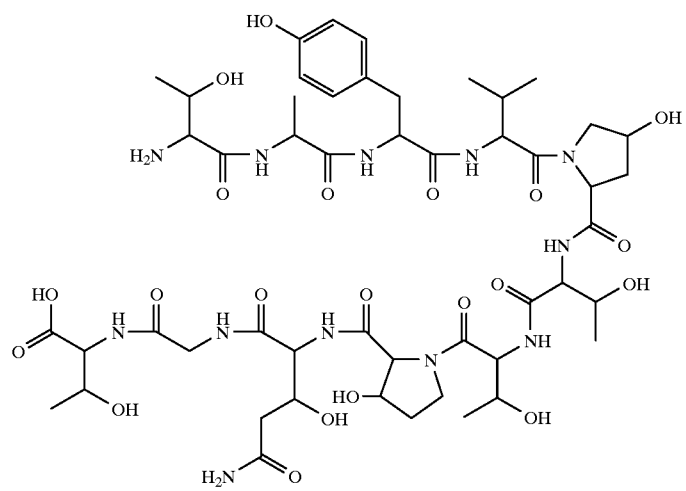
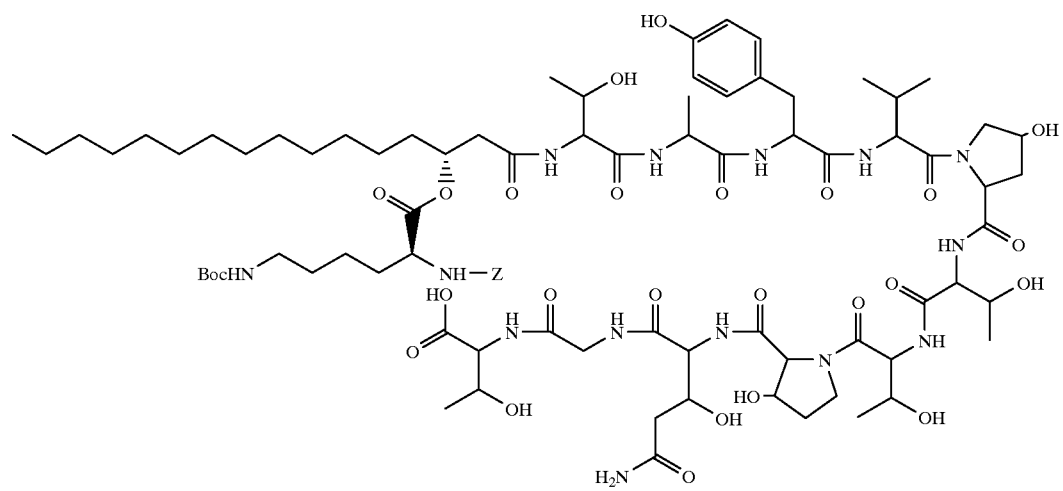

TABLE-continued
3 Upper sequence: SEQ ID NO: 7, Lower sequence: SEQ ID NO: 7.
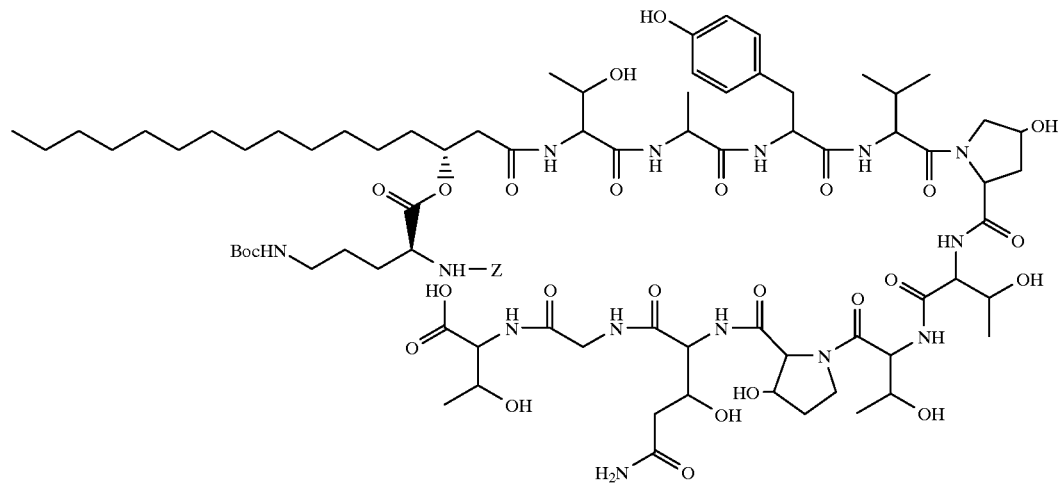
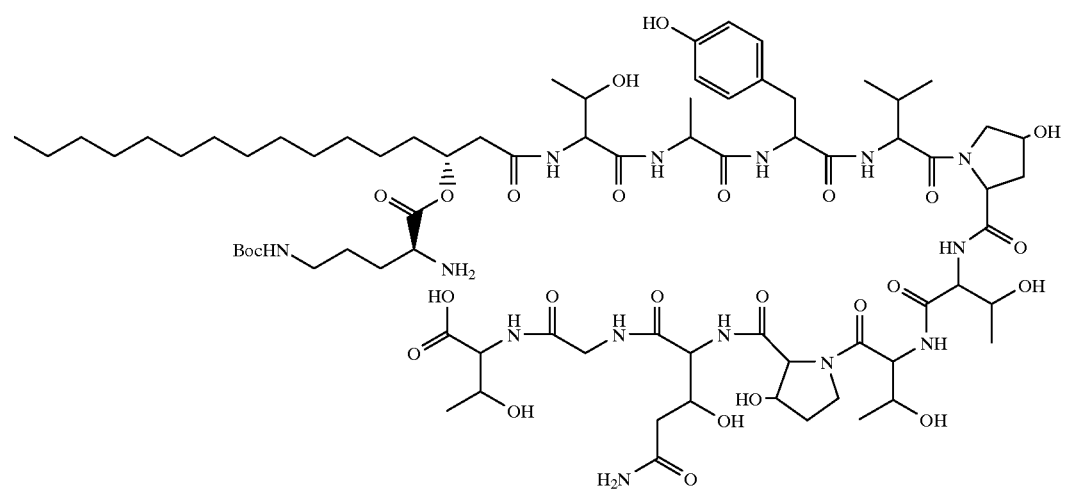
4 Upper sequence: SEQ ID NO: 7, Lower sequence: SEQ ID NO: 7.
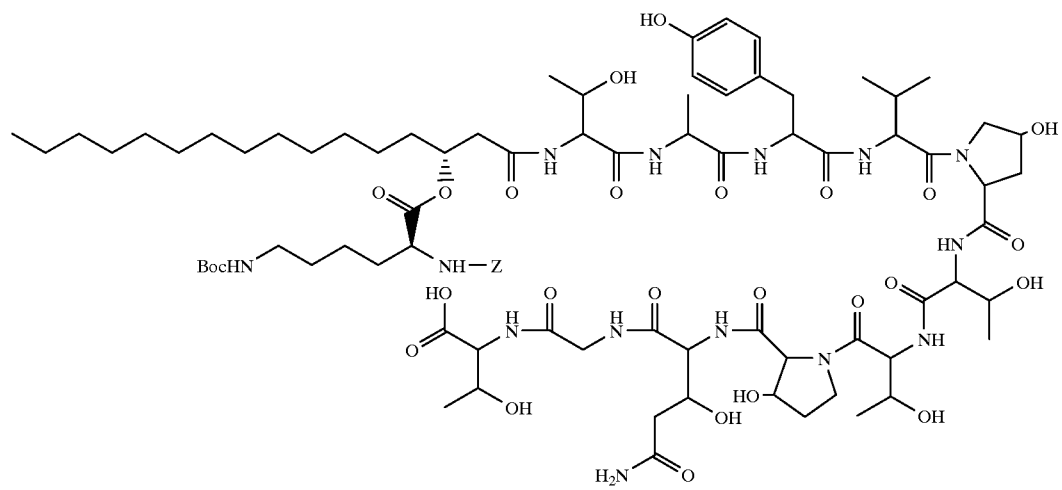

TABLE-continued
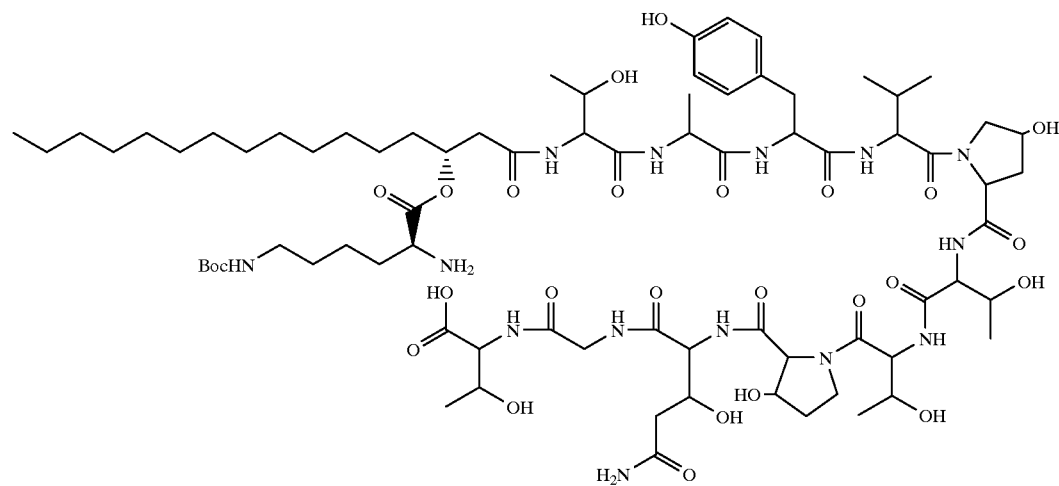
5  Upper sequence: SEQ ID NO: 7, Lower sequence: SEQ ID NO: 7.
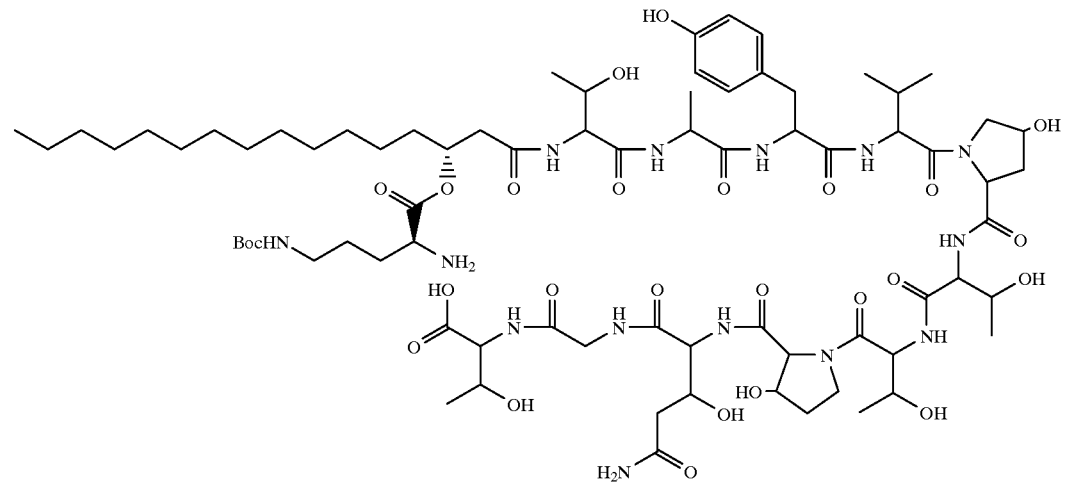
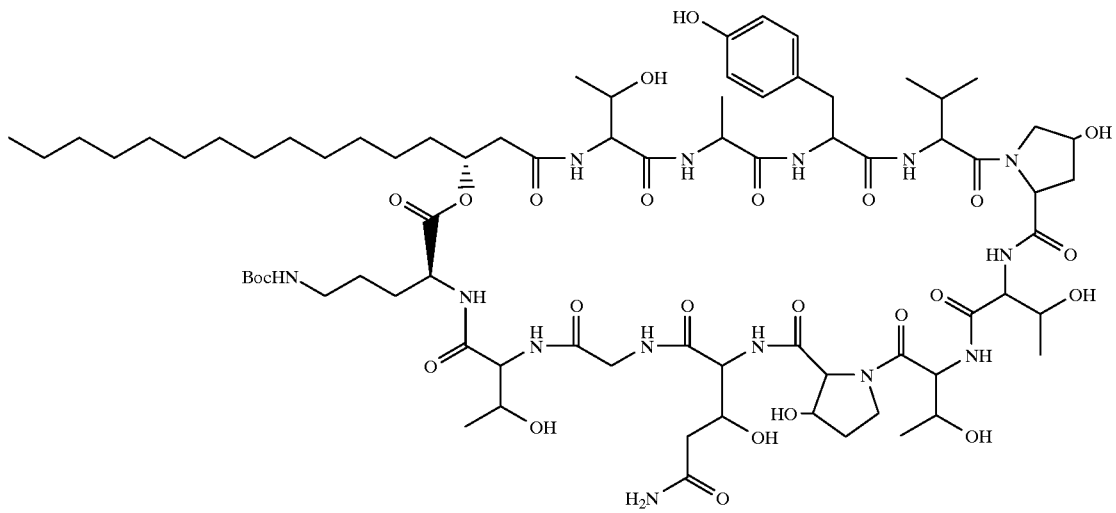

TABLE-continued
| 6 | Upper sequence: SEQ ID NO: 7, Lower sequence: SEQ ID NO: 4. |
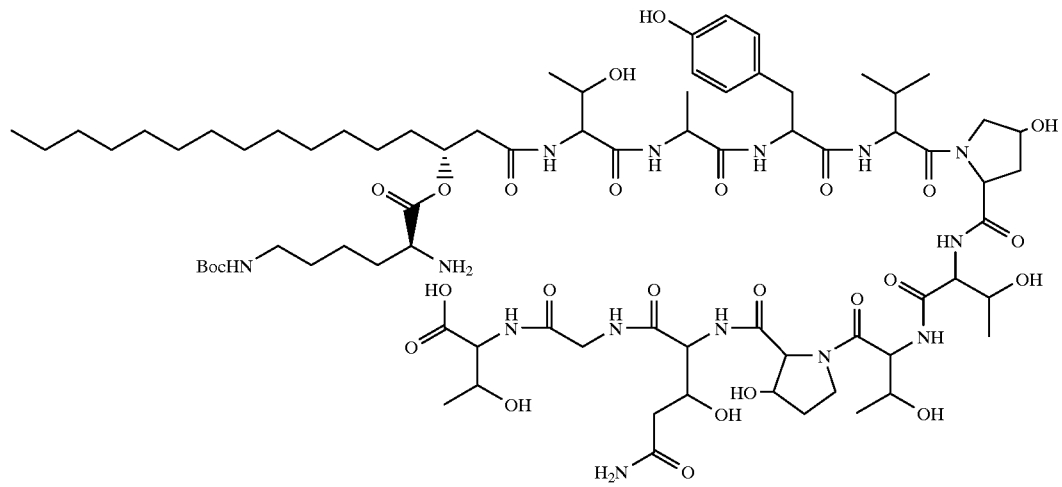
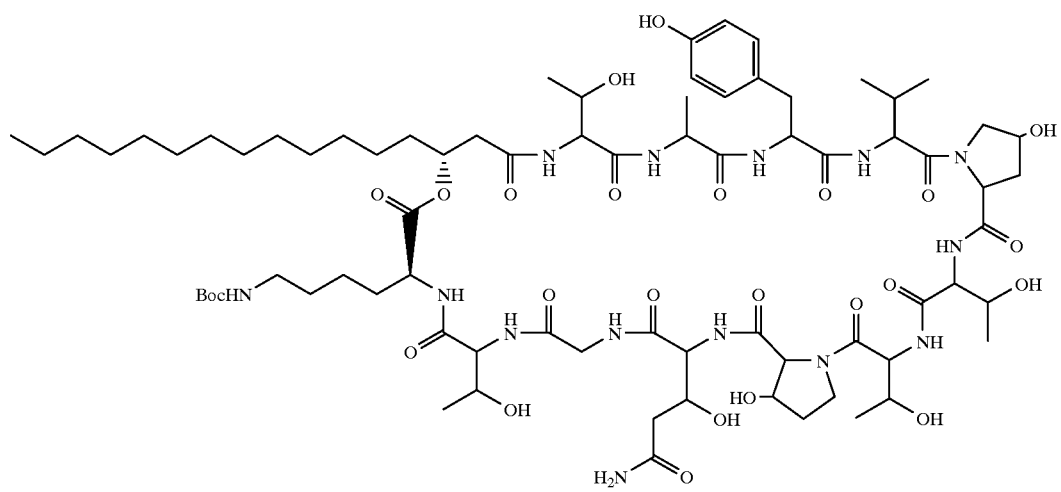
| 7 | Upper sequence: SEQ ID NO: 4, Lower sequence: SEQ ID NO: 6. |
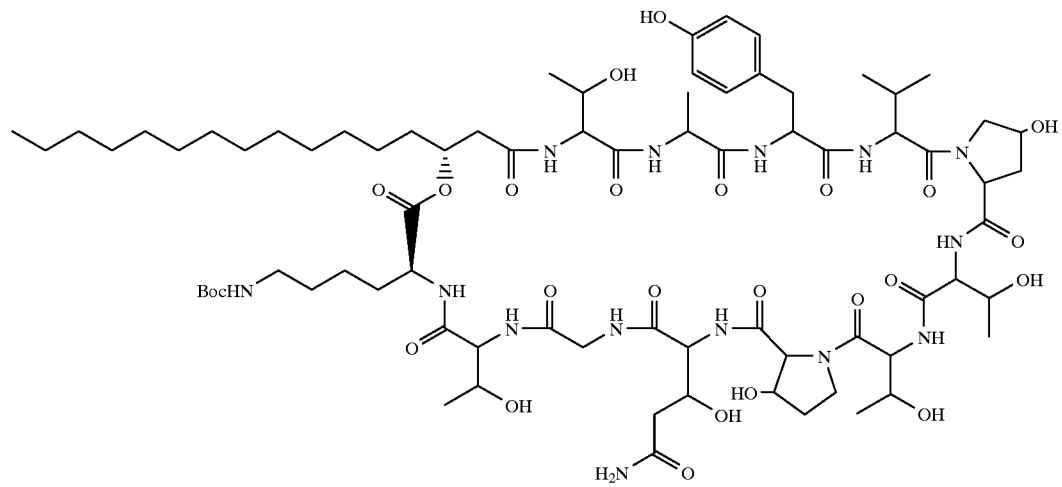

TABLE-continued
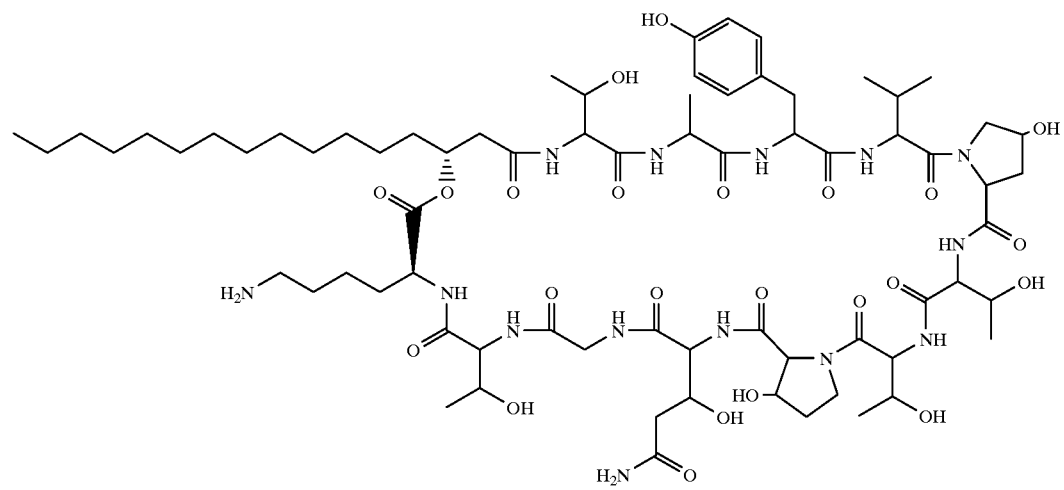
| 8 | Upper sequence: SEQ ID NO: 6, Lower sequence: SEQ ID NO: 4. |
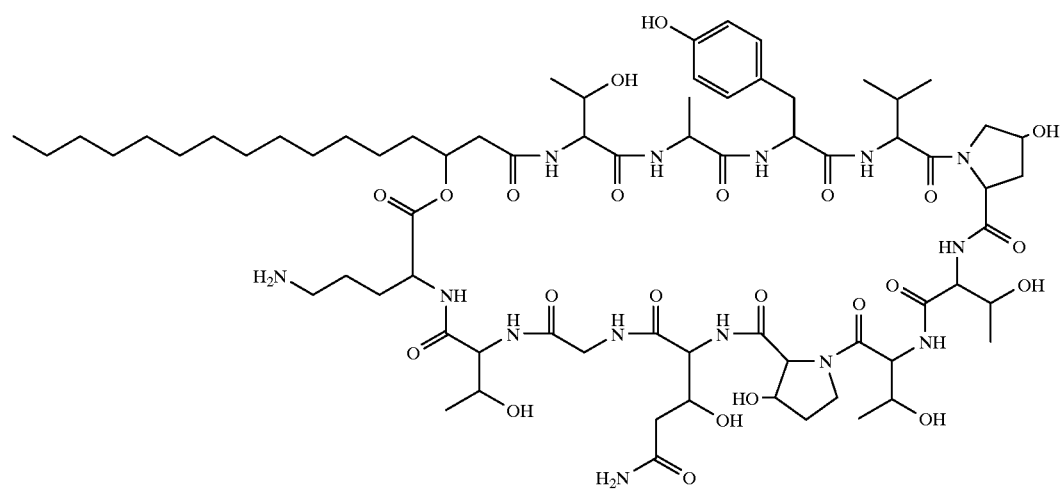
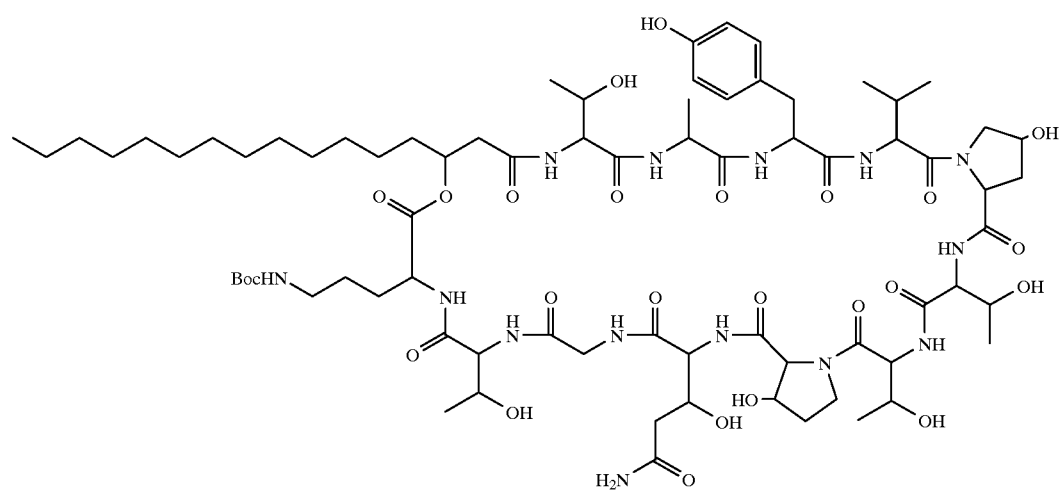

TABLE-continued
9     Upper sequence: SEQ ID NO: 5, Lower sequence: SEQ ID NO: 1.
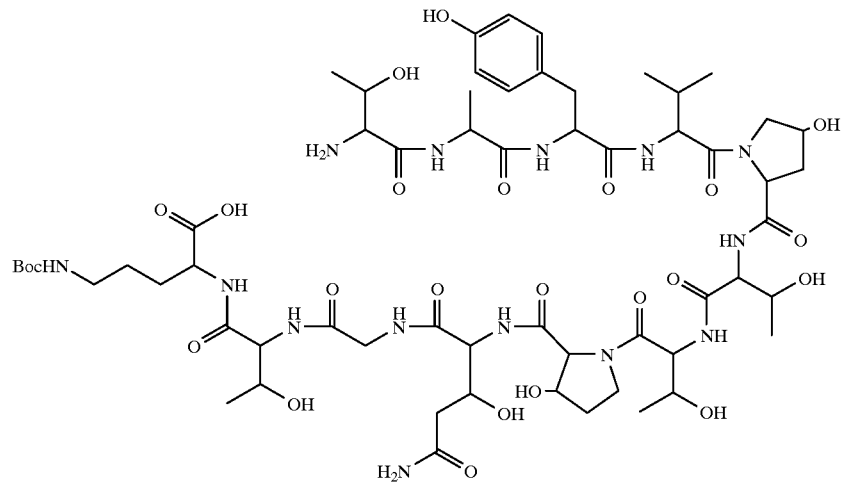
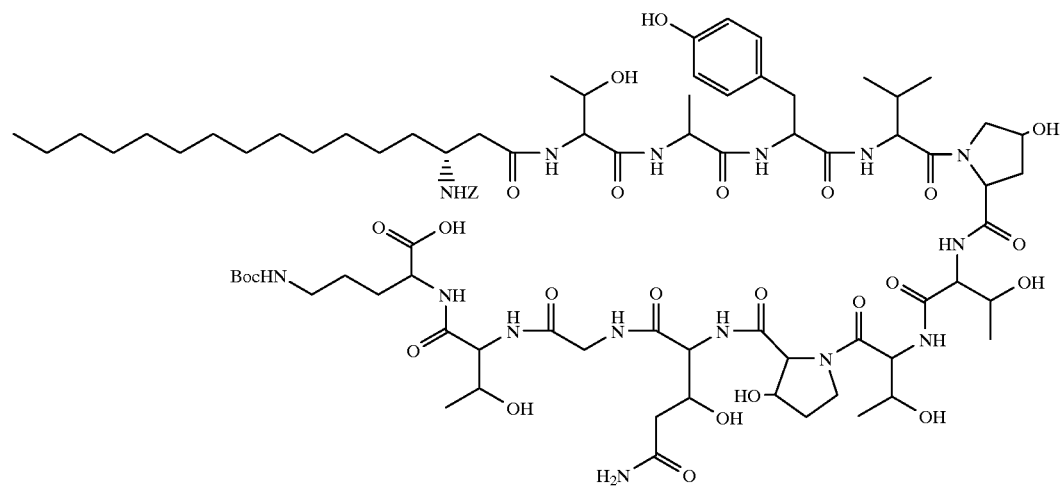
10     Upper sequence: SEQ ID NO: 8, Lower sequence: SEQ ID NO: 1.
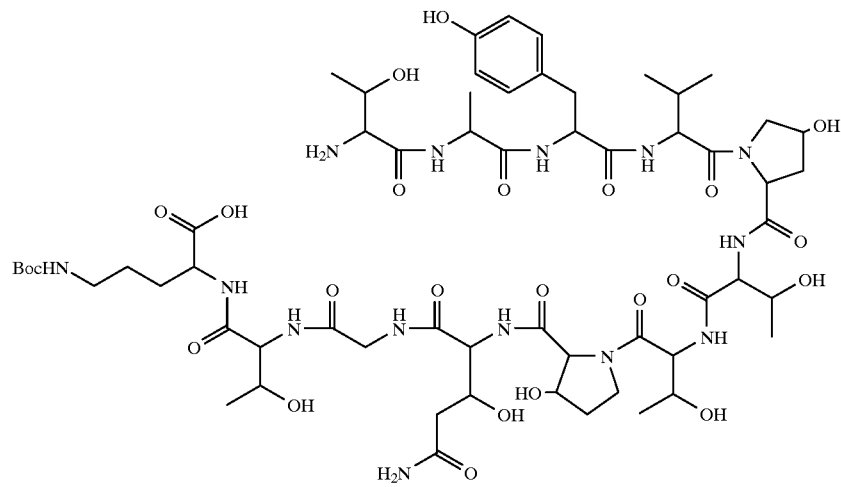

TABLE-continued
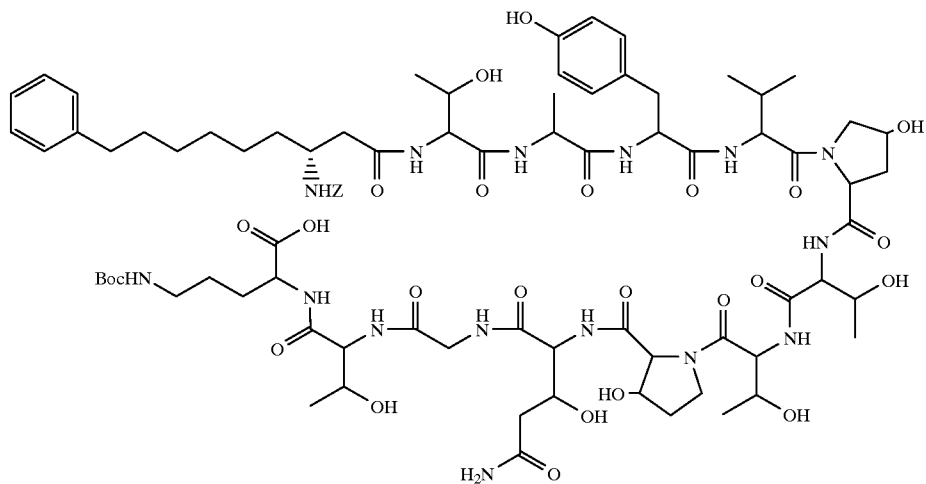
11  Upper sequence: SEQ ID NO: 1, Lower sequence: SEQ ID NO: 1.
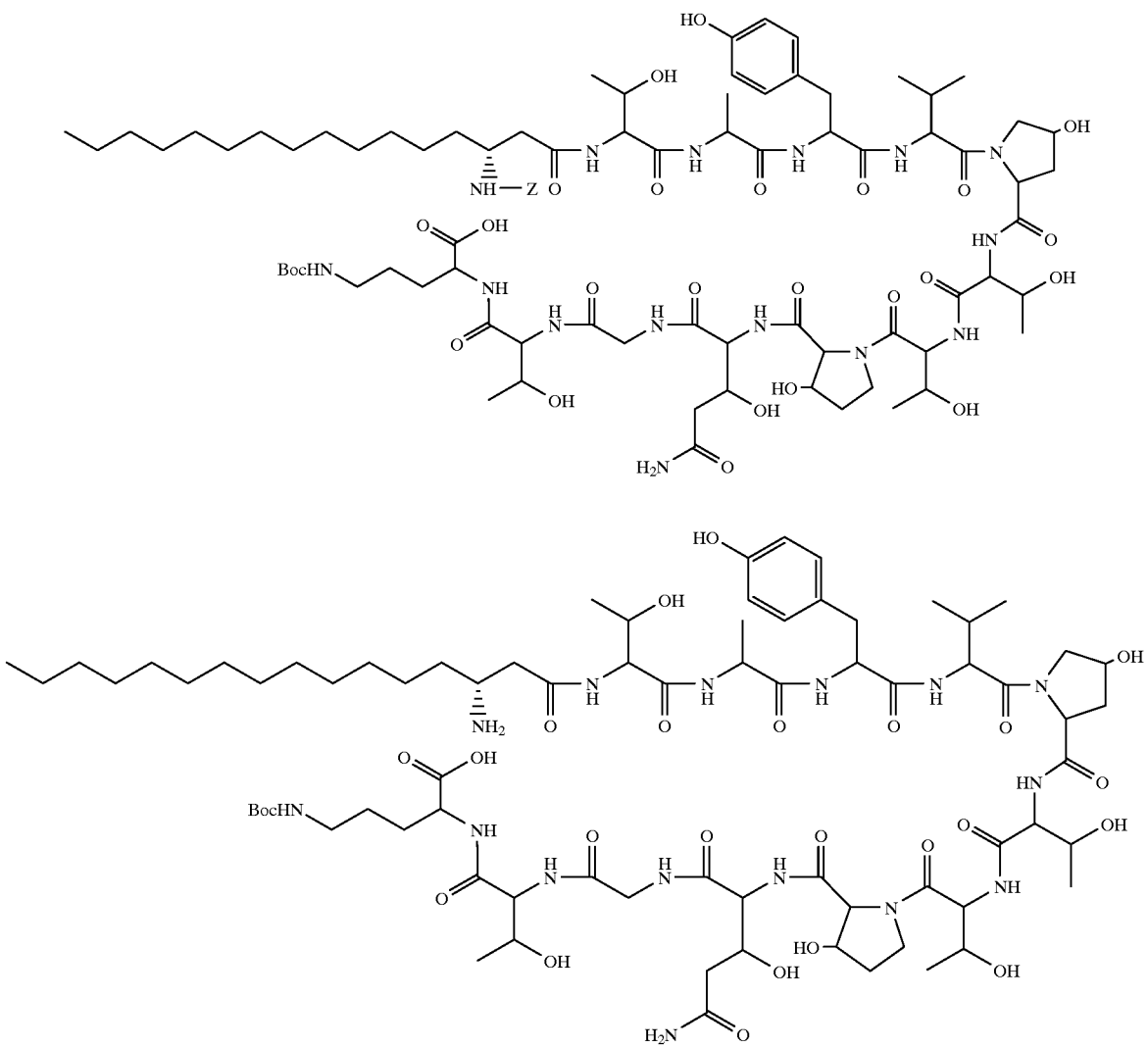

TABLE-continued
| 12 | Upper sequence: SEQ ID NO: 1, Lower sequence: SEQ ID NO: 1. |
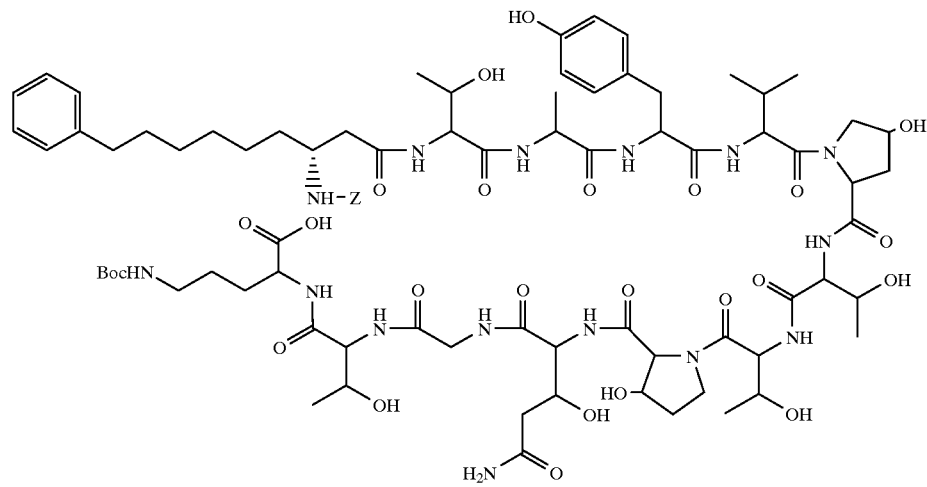
| 13 | Upper sequence: SEQ ID NO: 1, Lower sequence: SEQ ID NO: 4. |
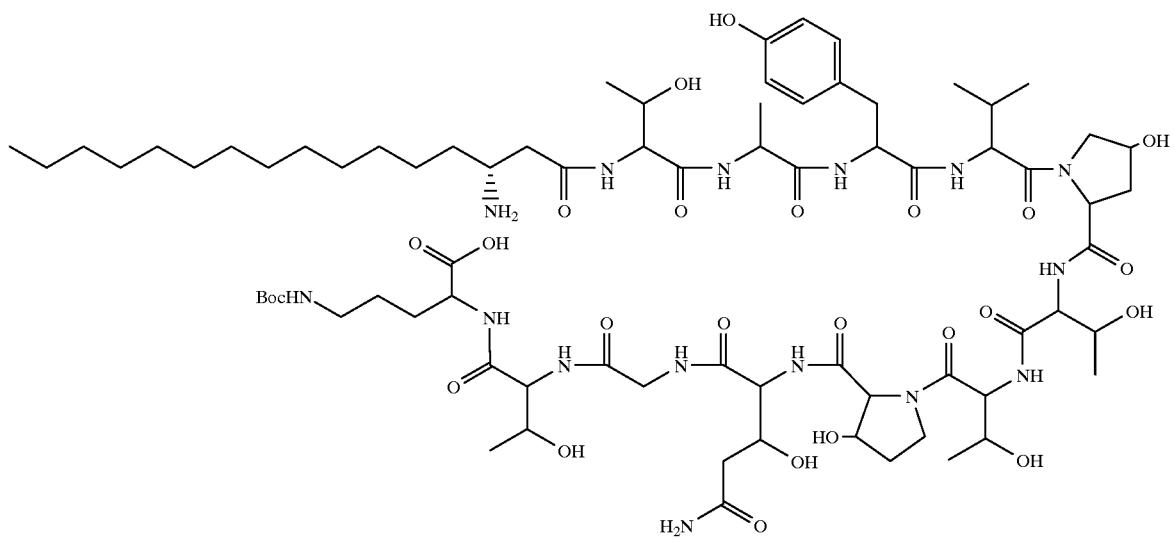

5,952,299
TABLE-continued
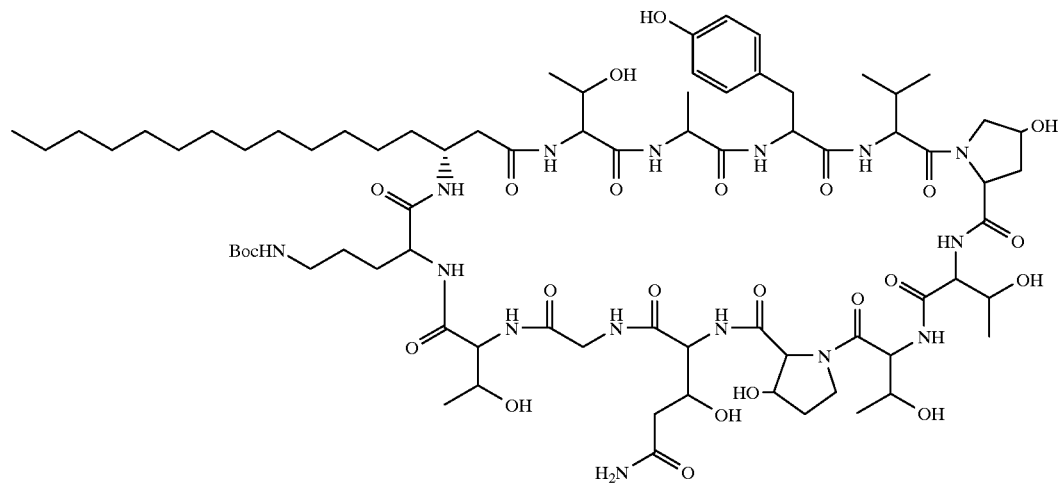
14     Upper sequence: SEQ ID NO: 1, Lower sequence: SEQ ID NO: 4.
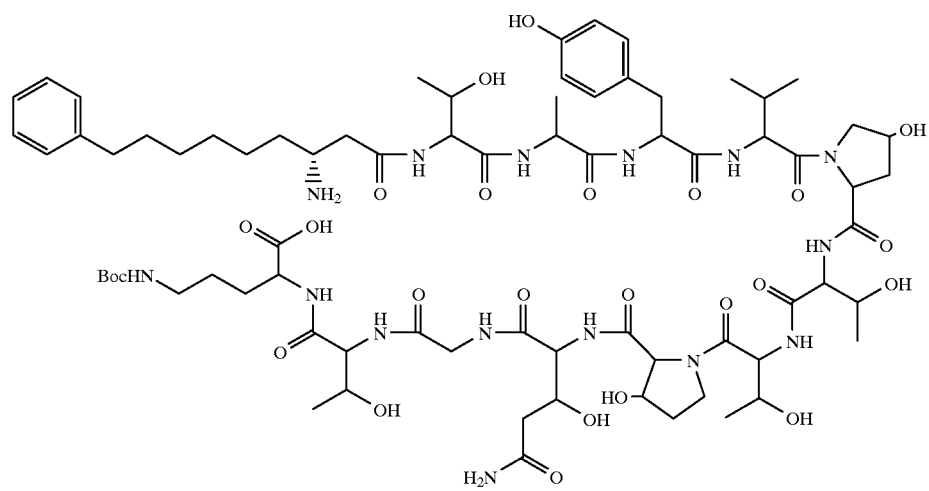
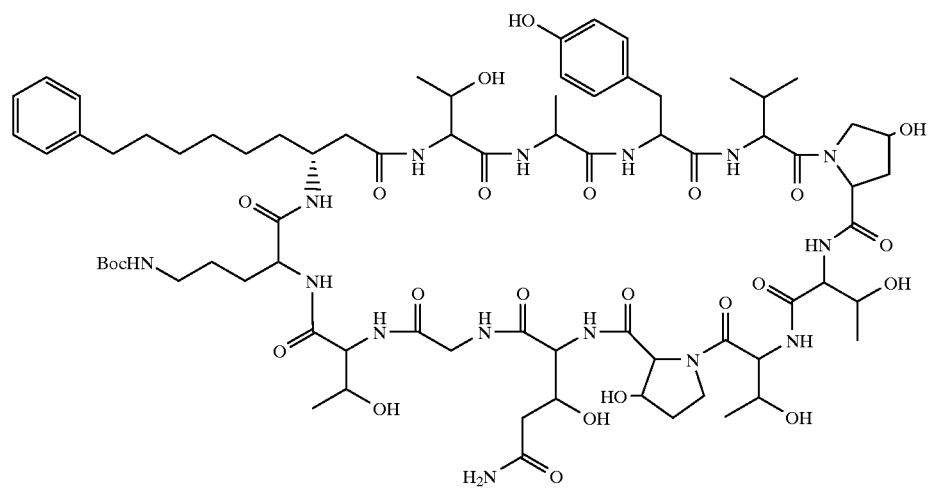

| | |
|---|---|
| 15 | Upper sequence: SEQ ID NO: 4, Lower sequence: SEQ ID NO: 6. |
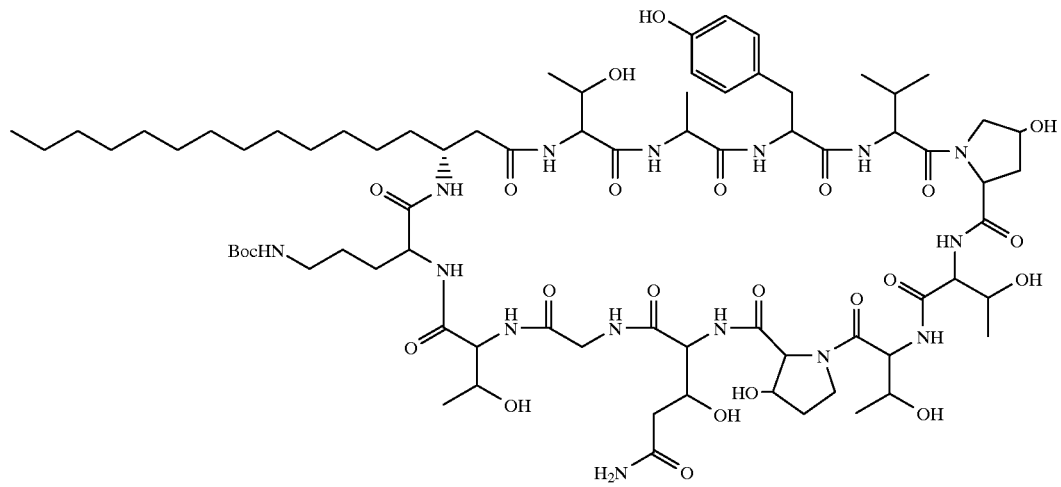
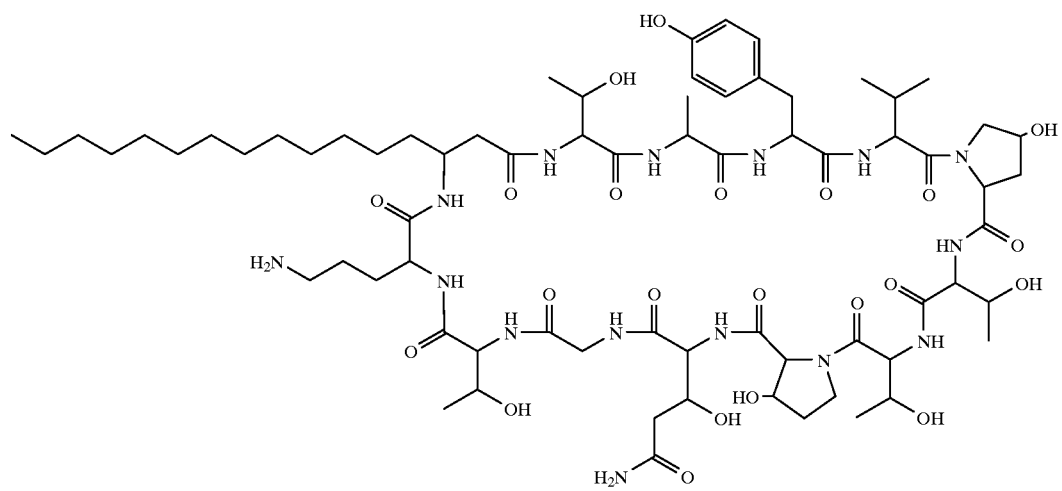
| | |
|---|---|
| 16 | Upper sequence: SEQ ID NO: 4, Lower sequence: SEQ ID NO: 6. |
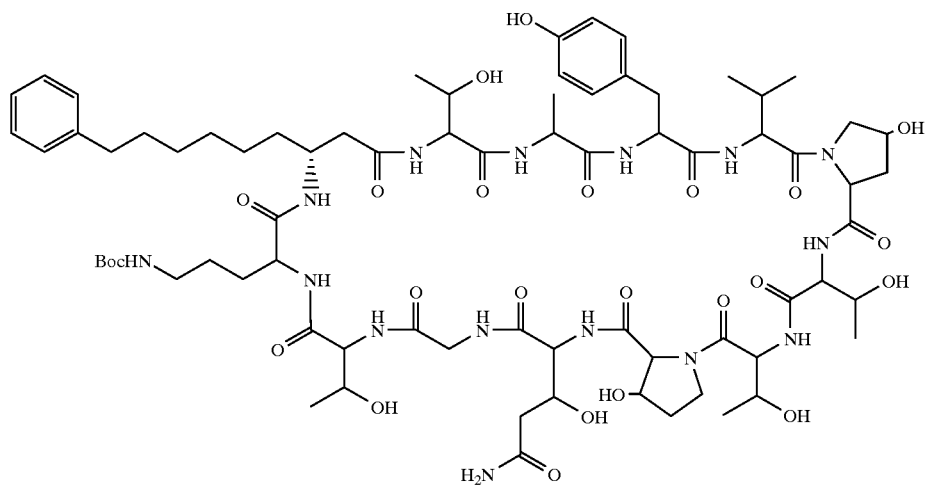

TABLE-continued

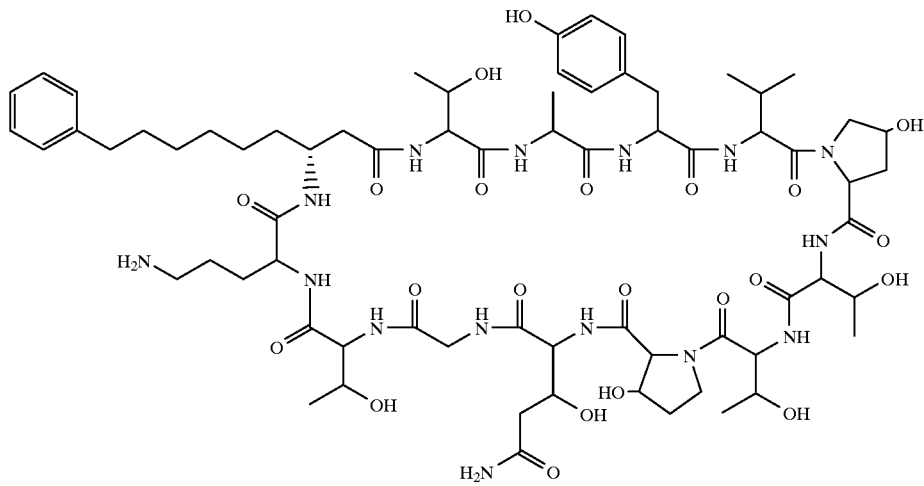

PREPARATION 5

A stock culture of Actinoplanes utahensis IFO-13244 is prepared and maintained on agar slant. A loopful of the slant culture was inoculated into a seed medium consisted of starch 1%, sucrose 1%, glucose 1%, cotton seed flour 1% peptone 0.5%, soy bean meal 0.5% and calcium carbonate 0.1%. The inoculated vegetative medium was incubated in a 225 ml wide mouth Erlenmeyer flask at 30° C. for about 72 hours on a rotary shaker.

This incubated vegetative medium was used directly to inoculate into a production medium consisted of sucrose 2%, peanut powder 1%, dipotassium hydrogenphosphate ($K_2HPO_4$) 0.12% potassium dihydrogenphosphate ($KH_2PO_4$) 0.05% and magnesium sulfate heptahydrate ($MgSO_4 \cdot 7H_2O$) 0.025%. The inoculated production medium was allowed to ferment in a 30 l jar fermentor at a temperature of 30° C. for about 80 hours. The fermentation medium was stirred with conventional agitators at 250 rpm and aerated at 20 l per minute. The vegetative mycelium was collected from the fermented broth by filtration and once washed with water. The washed mycelium was directly used to obtain Object compound.

Starting compound was prepared by the fermentation disclosed in EP 0 584 360 A1.

Starting compound was dissolved in 0.2M phosphate buffer (pH 7.8) at a concentration of 2.5 mg/ml. To a 2 l of the solution was added a 400 g wet weight of washed mycelium of Actinoplanes utahensis IFO-13244 obtained above. The reaction was carried out at 60° C. under for 20 hours. Reduction of Starting compound and increase of Object compound were measured using a HPLC equipped with a reverse phase column.

From a 5 g of Starting compound, a 1.3 g of Object compound was formed in the reaction mixture.

The reaction mixture described above was filtered with a filter aid. The mycelial cake was discarded. The filtrate thus obtained was passed through a column (350 ml) of YMC GEL ODS-AM 120-S50 (YMC Co., Ltd.) packed with water. The column was washed with 1 l of water and 2 l of 5% aqueous methanol and then eluted with 1 l of 30% aqueous methanol. The eluate was evaporated in vacuo to give a dry powder. The powder was dissolved in water (20 ml) and then applied on a column (350 ml) of YMC GEL ODS-AM 120-S50 packed with 10% aqueous acetonitrile containing 0.5% ammonium dihydrogenphosphate ($NH_4H_2PO_4$). The column was eluted with the same solvent system and elution was monitored by analytical HPLC, using a column of YMC-Pack ODS-AM AM303 (250×4.6 mm I.D., S-5 120A; YMC Co., Ltd.) and a solvent system of 12.5% aqueous acetonitrile containing 0.5% $NH_4H_2PO_4$ at a flow rate of 1 ml/minute, detecting with a UV monitor at 210 nm. The fractions containing Object compound were combined and evaporated in vacuo to remove acetonitrile and then passed through a column (180 ml) of YMC GEL ODS-AM 120-S50 packed with water. The column was washed with 1.8 l of water and 0.6 l of 5% aqueous methanol and then eluted with 0.6 l of 30% aqueous methanol. The eluate was concentrated in vacuo to remove methanol and lyophilized to give 1.15 g of Object compound as a white powder.

$^1$H NMR (400 MHz, $CD_3OD$, δ): 7.04 (2H, d, J=8 Hz), 6.70 (2H, d, J=8 Hz), 4.77 (1H, d, J=5 Hz), 4.63–3.83 (21H, m), 3.80 (1H, dd, J=4, 11 Hz), 3.19 (1H, dd, J=5, 14 Hz), 2.77 (1H, dd, J=11, 14 Hz), 2.46 (2H, M), 2.25 (2H, m), 2.11 (1H, m), 2.04 (2H, m), 1.23 (3H, d, J=6 Hz), 1.21 (3H, d, J=6 Hz), 1.17 (3H, d, J=6 Hz), 1.16 (3H, d, J=6 Hz), 0.97 (3H, d, J=6 Hz), 0.95 (3H, d, J=6 Hz)

FAB-MS (m/z): 1183 (M+H)$^+$

IR (KBr): 3300, 2980, 1655, 1540, 1455, 1235 cm$^{-1}$ $[\alpha]_D^{22}$=−33.7° (C=1.0, MeOH)

PREPARATION 6

To a solution of Starting compound (Object compound obtained in Example 8 shown below) (20 g) in water (500 ml) was added 2N sodium hydroxide solution (500 ml) and stirred under ice cooling for 1 hour. And then 2N hydrochloric acid solution (500 ml) was added to neutralize the reaction mixture containing the Compound A. To the neutralized solution was added 4 l of 1M phosphate buffer (pH 7.5) and 13 l of water and a 3 kg wet weight of washed mycelium of Actinoplanes utahensis IFO-13244 prepared according to a similar manner to that of Preparation 5. The reaction was carried out at 37° C. with stirring for 24 hours. Increase of Object compound was measured using a HPLC equipped with a reverse phase column.

From a 20 g of Starting compound, a 10 g of Object compound was formed in the reaction mixture.

The reaction mixture described above was filtrated with a filter aid. The mycelial cake was discarded. The filtrate thus obtained was passed through a column (500 ml) of DIAION HP-20 (Mitsubishi Chemical Industrials Ltd.) packed with water. The column was washed with water (1.5 l) and 20% aqueous methanol (1.5 l) and then eluted with 80% aqueous methanol (1.5 l). The eluate was evaporated in vacuo to give a dry powder. The powder was dissolved in water (100 ml) and then applied on a column (2 l) of YMC GEL ODS-AM 120-S50 (YMC Co., Ltd.) packed with 17.5% aqueous acetonitrile containing 0.5% $NH_4H_2PO_4$. The column was eluted with the same solvent system and elution was monitored by analytical HPLC, using a column of YMC-Pack ODS-AM AM303 (250 mm×4.6 mm I.D., S-5 120A; YMC Co., Ltd.) and solvent system of 17.5% aqueous acetonitrile containing 0.5% $NH_4H_2PO_4$ at a flow rate of 1 ml/minute detecting with a UV monitor at 210 nm. The fractions containing Object compound were combined and evaporated in vacuo to remove acetonitrile and then passed through a column (500 ml) of DIAION HP-20 packed with water. The column was washed with water (3 l) and 20% aqueous methanol (2 l) and then eluted with 80% aqueous methanol (2 l). The eluate was concentrated in vacuo to remove methanol and lyophilized to give 7.6 g of Object compound as a white powder.

$^1$H NMR (400 MHz, $CD_3OD$, δ): 7.03 (2H, d, J=8 Hz), 6.70 (2H, d, J=8 Hz), 4.78 (1H, d, J=5 Hz), 4.62–3.85 (22H, m), 3.80 (1H, dd, J=4, 11 Hz), 3.20 (1H, dd, J=5, 12 Hz), 3.05 (2H, m), 2.77 (1H, dd, J=10, 12 Hz), 2.47 (2H, m), 2.25 (2H, m), 2.05 (3H, m), 1.87 (1H, m), 1.71 (1H, m), 1.52 (2H, m), 1.42 (9H, m), 1.23 (3H, d, J=6 Hz), 1.21 (3H, d, J=6 Hz), 1.20 (3H, d, J=6 Hz), 1.18 (3H, d, J=6 Hz), 1.16 (3H, d, J=6 Hz), 0.97 (3H, d, J=6 Hz), 0.95 (3H, d, J=6 Hz)

FABMS (m/z): 1398 (M+H)$^+$

IR (KBr): 3305, 2975, 1655, 1520, 1455, 1250 cm$^{-1}$ $[\alpha]_D^{25}$=−20.8° (C=1.0, MeOH)

EXAMPLE 1

To a solution of (3R)-3-[$N^2$-benzyloxycarbonyl-$N^5$-tert-butoxycarbonyl-L-ornithyl]oxy-hexadecanoic acid (31 mg) in dichloromethane (0.5 ml) was added pivaloyl chloride (6.15 ul) and triethylamine (6.97 ul) at 0° C. and the mixture was stirred for 1 hour at same temperature. The reaction mixture was droped into a solution of Starting compound (Object compound obtained in Preparation 5) (59 mg) in N,N-dimethylformamide (1.5 ml) and triethylamine (6.97 ul) at 0° C. and the reaction mixture was stirred for 4 hours at room temperature. After the solvent was evaporated in vacuo the residue was purified by ODS open column to give Object compound (39 mg).

$^1$H NMR (300 MHz, $CD_3OD$, δ): 7.32 (5H, m), 7.00 (2H, d, J=8.5 Hz), 6.68 (2H, d, J=8.5 Hz), 5.22 (1H, m), 5.07 (2H, s), 4.66 (1H, d, J=5 Hz), 4.63–3.8 (22H, m), 3.73 (1H, dd, J=4, 11 Hz), 3.02 (3H, m), 2.78 (1H, dd, J=9, 14 Hz), 2.53 (2H, m), 2.45 (2H, d, J=7 Hz), 2.26 (2H, m), 2.00 (3H, m), 1.79 (1H, m), 1.73–1.45 (5H, m), 1.43 (9H, s), 1.4–1.2 (37H, m), 0.92 (9H, m)

FABMS (m/z): 1808 (M+Na)$^+$

IR (KBr): 3305, 2925, 1735, 1655, 1515, 1455, 1245 cm$^{-1}$ $[\alpha]_D^{22}$=−6.2° (C=2.0, MeOH)

EXAMPLE 2

The Object compound was obtained according to a similar manner to that of Example 1.

$^1$H NMR (400 MHz, $CD_3OD$, δ): 7.33 (5H, m), 7.02 (2H, d, J=8.5 Hz), 6.71 (2H, d, J=8.5 Hz), 5.23 (1H, m), 5.09 (2H, s), 4.68 (1H, d, J=5 Hz), 4.65–3.70 (23H, m), 3.02 (3H, m), 2.81 (1H, dd, J=9, 14 Hz), 2.54 (2H, m), 2.48 (2H, br d, J=7 Hz), 2.26 (2H, m), 2.02 (3H, m), 1.78 (1H, m), 1.62 (3H, m), 1.42 (9H, s), 1.5–1.2 (38H, m), 1.20 (3H, d, J=7 Hz), 0.95 (3H, d, J=7 Hz), 0.93 (3H, d, J=7 Hz), 0.90 (3H, t, J=7 Hz)

FABMS (m/z): 1822 (M+Na)$^+$

IR (KBr): 3305, 2925, 1730, 1655, 1540, 1455, 1250 cm$^{-1}$ $[\alpha]_D^{22}$=−6.5° (C=1.0, MeOH)

EXAMPLE 3

To a solution of Starting compound (Object compound obtained in Example 1) (39 mg) in methanol (3 ml) was added 10% palladium-carbon (40 mg) and the mixture was hydrogenated (1 atm) at room temperature for 6 hours. The reaction mixture was filtered and the filtrate was evaporated in vacuo to give Object compound (32.4 mg).

$^1$H NMR (400 MHz, $CD_3OD$, δ): 7.02 (2H, d, J=8.5 Hz), 6.72 (2H, d, J=8.5 Hz), 5.31 (1H, m), 4.72 (1H, d, J=5 Hz), 4.6–3.8 (22H, m), 3.75 (1H, m), 3.09 (2H, m), 3.00 (1H, dd, J=6, 14 Hz), 2.80 (1H, dd, J=9, 14 Hz), 2.6 (2H, m), 2.47 (2H, d, J=7 Hz), 2.27 (2H, m), 2.03 (3H, m), 1.95–1.5 (6H, m), 1.44 (9H, s), 1.4–1.18 (34H, m), 1.15 (3H, d, J=7 Hz), 0.95 (3H, d, J=7 Hz), 0.92 (3H, d, J=7 Hz), 0.89 (3H, t, J=7 Hz)

FABMS (m/z): 1652 (M+H)$^+$

IR (KBr): 3315, 2925, 1745, 1655, 1520, 1455, 1250 cm$^{-1}$ $[\alpha]_D^{22}$=+0.7° (C=1.62, MeOH)

EXAMPLE 4

The Object compound was obtained according to a similar manner to that of Example 3.

$^1$H NMR (400 MHz, $CD_3OD$, δ): 7.02 (2H, d, J=8.5 Hz), 6.72 (2H, d, J=8.5 Hz), 5.31 (1H, m), 4.75–3.7 (24H, m), 3.04 (3H, m), 2.80 (1H, m), 2.54 (2H, m), 2.47 (2H, br d, J=7 Hz), 2.27 (2H, m), 2.03 (3H, m), 1.43 (9H, s), 1.9–1.2 (42H, m), 1.15 (3H, d, J=7 Hz), 0.95 (3H, d, J=7 Hz), 0.93 (3H, d, J=7 Hz), 0.90 (3H, t, J=7 Hz)

FABMS (m/z): 1666 (M+H)$^+$

IR (KBr): 3310, 2925, 1740, 1655, 1515, 1455, 1250 cm$^{-1}$ $[\alpha]_D^{22}$=+0.3° (C=1.0, MeOH)

EXAMPLE 5

To a solution of Starting compound (Object compound obtained in Example 3) (32.4 mg) in N,N-dimethylformamide (20 ml) was added 1-ethyl-3-(3-dimethylaminopropyl)carbodiimide-hydrochloride (WSCD.HCl) (7.7 mg) and 1-hydroxy benzotriazole (HOBT) (5.4 mg) at room temperature. After the reaction mixture was stirred for 2 hours, WSCD.HCl (3.83 mg) and HOBT (2.7 mg) were added to the solution and stirred for 2 hours at room temperature. After the solvent was evaporated in vacuo the residue was purified by ODS open column to give Object compound (22 mg).

$^1$H NMR (400 MHz, $CD_3OD$, δ): 7.08 (2H, d, J=8 Hz), 6.84 (2H, d, J=8 Hz), 5.12 (1H, m), 4.97 (1H, d, J=4 Hz), 4.69 (1H, s), 4.65–3.84 (20H, m), 3.74 (2H, br s), 3.05 (2H, m), 2.90 (2H, d, J=8 Hz), 2.60–1.80 (11H, m), 1.70–1.43 (4H, m), 1.43 (9H, s), 1.40–1.16 (34H, m), 1.15 (3H, d, J=6 Hz), 0.9 (9H, m)

FABMS (m/z): 1656 (M+Na)$^+$

IR (KBr): 3305, 2930, 1735, 1655, 1515, 1455, 1250 cm$^{-1}$ $[\alpha]_D^{22}$=+4.5° (C=1.0, MeOH)

EXAMPLE 6

The Object compound was obtained according to a similar manner to that of Example 5.

$^1$H NMR (400 MHz, CD$_3$OD, δ): 7.11 (2H, d, J=8 Hz), 6.86 (2H, d, J=8 Hz), 5.09 (1H, m), 4.98 (1H, d, J=3 Hz), 4.73–3.85 (21H, m), 3.72 (2H, br s), 3.05 (2H, m), 2.90 (2H, d, J=8 Hz), 2.63–2.17 (6H, m), 2.13–1.75 (5H, m), 1.72–1.15 (40H, m), 1.14 (3H, d, J=7 Hz), 0.90 (3H, d, J=7 Hz), 0.87 (3H, d, J=7 Hz), 0.86 (3H, t, J=7 Hz)

FABMS (m/z): 1670 (M+Na)$^+$

IR (KBr): 3335, 2925, 1735, 1655, 1515, 1455, 1250 cm$^{-1}$ $[\alpha]_D^{22}$=+6.0° (C=1.0, MeOH)

EXAMPLE 7

A solution of Starting compound (Object compound obtained in Example 6) (42 mg) in trifluoroacetic acid (0.5 ml) was stirred at 0° C. for 30 minutes. After the solvent was evaporated in vacuo, the residue was purified by preparative HPLC to give Object compound (20.1 mg).

$^1$H NMR (400 MHz, CD$_3$OD, δ): 7.09 (2H, d, J=8 Hz), 6.88 (2H, d, J=8 Hz), 5.12 (1H, m), 5.00 (1H, br s), 4.67–3.85 (21H, m), 3.73 (1H, br s), 3.64 (1H, br d, J=11 Hz), 2.96 (3H, m), 2.85 (1H, m), 2.65–2.18 (6H, m), 2.13–1.85 (5H, m), 1.72–1.25 (40H, m), 1.14 (3H, d, J=7 Hz), 0.88 (9H, m)

FABMS (m/z): 1548 (M+H)$^+$

IR (KBr): 3310, 2930, 1740, 1660, 1520, 1455, 1085 cm$^{-1}$ $[\alpha]_D^{22}$=+11.6° (C=1.0, MeOH)

EXAMPLE 8

To a solution of Starting compound (20 g) prepared by the fermentation disclosed in EP 0 584 360 A1 in dioxane (250 ml) and water (250 ml) was added di-tert-butyl-dicarbonate (6 g) and triethylamine (2 ml) at a room temperature and stirred for 2 hours.

After solvent was evaporated in vacuo, 500 ml of water was added. The solution was passed through a column (1 l) of YMC GEL ODS-AM 120-S50 (YMC Co., Ltd.) packed with water. The column was washed with 3 l of water and 3 l of 50% aqueous methanol and then eluted with 3 l of 95% aqueous methanol. The eluate was concentrated in vacuo to remove methanol and lyophilized to give 20 g of Object compound as a white powder.

$^1$H NMR (400 MHz, CD$_3$OD, δ): 7.08 (2H, d, J=8 Hz), 6.84 (2H, d, J=8 Hz), 5.12 (1H, m), 4.97 (1H, d, J=4 Hz), 4.69 (1H, s), 4.65–3.84 (20H, m), 3.74 (2H, br s), 3.05 (2H, m), 2.90 (2H, d, J=8 Hz), 2.60–1.80 (11H, m), 1.70–1.43 (4H, m), 1.43 (9H, s), 1.40–1.16 (34H, m), 1.15 (3H, d, J=6 Hz), 0.90 (9H, m)

FABMS (m/z): 1634 (M+H)$^+$

IR (KBr): 3305, 2930, 1735, 1655, 1515, 1455, 1250 cm$^{-1}$ $[\alpha]_D^{24}$=+5.9° (C=1.0, MeOH)

EXAMPLE 9

To a solution of (3R)-3-benzyloxycarbonylamino-hexadecanoic acid (29 mg) in dichloromethane (1.0 ml) was added pivaloyl chloride (8.82 ul) and triethylamine (9.98 ul) at 0° C. and the mixture was stirred for 1 hour at same temperature. The reaction mixture was droped into a solution of Starting compound (Object compound obtained in Preparation 6) (100 mg) in N,N-dimethylformamide (1.0 ml) and triethylamine (9.98 ul) at 0° C. and the reaction mixture was stirred for 4 hours at room temperature. After the solvent was evaporated in vacuo the residue was purified by ODS open column to give Object compound (70 mg).

$^1$H NMR (400 MHz, CD$_3$OD, δ): 7.33 (5H, m), 7.02 (2H, d, J=8 Hz), 6.71 (2H, d, J=8 Hz), 5.06 (2H, m), 4.69 (1H, d, J=5 Hz), 4.63–3.83 (23H, m), 3.75 (1H, m), 3.05 (2H, t, J=7 Hz), 3.00 (1H, dd, J=7, 14 Hz), 2.82 (1H, dd, J=9, 14 Hz), 2.45 (4H, m), 2.27 (2H, m), 2.02 (3H, m), 1.89 (1H, m), 1.74 (1H, m), 1.42 (9H, s), 1.64–1.15 (41H, m), 0.95 (3H, d, J=7 Hz), 0.92 (3H, d, J=7 Hz), 0.90 (3H, t, J=7 Hz)

FABMS (m/z): 1807 (M+Na)$^+$

IR (KBr): 3320, 2925, 1660, 1540, 1455, 1255 cm$^{-1}$ $[\alpha]_D^{24}$=+3.1° (C=1.0, MeOH)

EXAMPLE 10

The Object compound was obtained according to a similar manner to that of Example 9.

$^1$H NMR (400 MHz, CD$_3$OD, δ): 7.35–7.2 (7H, m), 7.15 (3H, m), 7.02 (2H, d, J=8 Hz), 6.72 (2H, d, J=8 Hz), 5.05 (2H, m), 4.69 (1H, d, J=5 Hz), 4.65–3.8 (23H, m), 3.74 (1H, m), 3.05 (2H, t, J=7 Hz), 3.00 (1H, dd, J=7, 14 Hz), 2.81 (1H, dd, J=9, 14 Hz), 2.58 (2H, m), 2.45 (4H, m), 2.26 (2H, m), 2.02 (3H, m), 1.89 (1H, m), 1.74 (1H, m), 1.42 (9H, s), 1.65–1.16 (27H, m), 0.95 (3H, d, J=7 Hz), 0.92 (3H, d, J=7 Hz)

FABMS (m/z): 1785 (M+Na)$^+$

IR (KBr): 3325, 2930, 1690, 1535, 1455, 1250 cm$^{-1}$ $[\alpha]_D^{23}$=+3.9° (C=1.0, MeOH)

EXAMPLE 11

To a solution of Starting compound (Object compound obtained in Example 9) (70 mg) in methanol (6 ml) was added 10% palladium-carbon (100 mg) and the mixture was hydrogenated (1 atm) at room temperature for 6 hours. The reaction mixture was filtered and the filtrate was evaporated in vacuo to give Object compound (46.1 mg).

$^1$H NMR (400 MHz, CD$_3$OD, δ): 7.03 (2H, d, J=8 Hz), 6.72 (2H, d, J=8 Hz), 4.73 (1H, d, J=5 Hz), 4.62–3.83 (22H, m), 3.75 (1H, m), 3.52 (1H, m), 3.05 (3H, m), 2.80 (1H, dd, J=9, 14 Hz), 2.75–2.4 (4H, m), 2.28 (2H, m), 2.05 (3H, m), 1.88 (1H, m), 1.42 (9H, s), 1.8–1.15 (42H, m), 0.97 (3H, d, J=7 Hz), 0.94 (3H, d, J=7 Hz), 0.90 (3H, t, J=7 Hz)

FABMS (m/z): 1651 (M+H)$^+$

IR (KBr): 3325, 2930, 1665, 1515, 1455, 1250 cm$^{-1}$ $[\alpha]_D^{22}$=−1.15° (C=1.83, MeOH)

EXAMPLE 12

The Object compound was obtained according to a similar manner to that of Example 11.

$^1$H NMR (400 MHz, CD$_3$OD, δ): 7.22 (2H, m), 7.15 (3H, m), 7.03 (2H, d, J=8 Hz), 6.72 (2H, d, J=8 Hz), 4.72 (1H, d, J=5 Hz), 4.65–3.8 (22H, m), 3.74 (1H, m), 3.48 (1H, m), 3.05 (3H, m), 2.80 (1H, dd, J=9, 14 Hz), 2.7–2.4 (6H, m), 2.28 (2H, m), 2.04 (3H, m), 1.89 (1H, m), 1.42 (9H, s), 1.8–1.3 (13H, m), 1.22–1.16 (15H, m), 0.97 (3H, d, J=7 Hz), 0.94 (3H, d, J=7 Hz)

FABMS (m/z): 1629 (M+H)$^+$

IR (KBr): 3305, 2935, 1670, 1520, 1455, 1250 cm$^{-1}$ $[\alpha]_D^{22}$=−1.5° (C=1.0, MeOH)

EXAMPLE 13

To a solution of Starting compound (Object compound obtained in Example 11) (46 mg) in dimethylformamide (28 ml) was added WSCD.HCl (10.7 mg) and HOBT (7.5 mg) at room temperature. After the reaction mixture was stirred for 2 hours, WSCD.HCl (5.3 g) and HOBT (3.8 mg) were added to the solution and stirred for 2 hours at room temperature. After the solvent was evaporated in vacuo, the residue was purified by ODS open column to give Object compound (19.4 mg).

$^1$H NMR (400 MHz, CD$_3$OD, δ): 7.06 (2H, d, J=8 Hz), 6.78 (2H, d, J=8 Hz), 4.86–3.6 (25H, m), 3.04 (3H, m), 2.90 (1H, dd, J=9, 14 Hz), 2.48 (2H, m), 2.33 (1H, dd, J=9, 14 Hz), 2.25 (2H, m), 2.02 (3H, m), 1.43 (9H, s), 1.6–1.2 (44H, m), 1.19 (3H, d, J=7 Hz), 0.92 (3H, d, J=7 Hz), 0.91 (3H, d, J=7 Hz), 0.90 (3H, t, J=7 Hz)

FABMS (m/z): 1633 (M+H)$^+$

IR (KBr): 3310, 2925, 1655, 1520, 1450, 1250 cm$^{-1}$ $[α]_D^{22}$=+3.3° (C=0.95, MeOH)

EXAMPLE 14

The Object compound was obtained according to a similar manner to that of Example 13.

$^1$H NMR (400 MHz, CD$_3$OD, δ): 7.22 (2H, m), 7.15 (3H, m), 7.05 (2H, d, J=8 Hz), 6.78 (2H, d, J=8 Hz), 4.63–3.6 (25H, m), 3.04 (3H, m), 2.90 (1H, dd, J=9, 14 Hz), 2.58 (2H, m), 2.47 (4H, m), 2.33 (1H, dd, J=9, 14 Hz), 2.25 (2H, m), 2.02 (3H, m), 1.42 (9H, s), 1.65–1.15 (30H, m), 0.92 (3H, d, J=7 Hz), 0.89 (3H, d, J=7 Hz)

FABMS (m/z): 1611 (M+H)$^+$

IR (KBr): 3310, 2935, 1655, 1515, 1450, 1250 cm$^{-1}$ $[α]_D^{22}$=+3.1° (C=1.69, MeOH)

EXAMPLE 15

A solution of Starting compound (Object compound obtained in Example 13) (19.4 mg) in trifluoroacetic acid (0.5 ml) was stirred at 0° C. for 30 minutes. After the solvent was evaporated in vacuo, the residue was purified by preparative HPLC to give Object compound (19.4 mg).

$^1$H NMR (400 MHz, CD$_3$OD, δ): 7.05 (2H, d, J=8 Hz), 6.84 (2H, d, J=8 Hz), 4.95 (1H, d, J=4 Hz), 4.74 (1H, br s), 4.64 (3H, m), 4.5–3.8 (18H, m), 3.69 (2H, m), 2.94 (4H, m), 2.52–2.15 (5H, m), 2.04 (3H, m), 1.75 (1H, s), 1.65–1.2 (43H, m), 1.17 (3H, d, J=7 Hz), 0.89 (3H, t, J=7 Hz), 0.89 (3, d, J=7 Hz), 0.87 (3H, d, J=7 Hz)

FABMS (m/z): 1533 (M+H)$^+$

IR(KBr): 3310, 2930, 1660, 1520, 1455, 1085 cm$^{-1}$ $[α]_D^{22}$=+16.6° (C=0.5, MeOH)

EXAMPLE 16

The Object compound was obtained according to a similar manner to that of Example 15.

$^1$H NMR (400 MHz, CD$_3$OD, δ): 7.22 (2H, m), 7.14 (3H, m), 7.04 (2H, d, J=8 Hz), 6.84 (2H, d, J=8 Hz), 4.95 (1H, d, J=4 Hz), 4.73 (1H, br s), 4.65 (2H, m), 4.5–3.8 (19H, m), 3.70 (2H, m), 2.94 (4H, m), 2.57 (2H, m), 2.48 (1H, dd, J=8, 14 Hz), 2.43–2.18 (5H, m), 2.02 (4H, m), 1.75 (1H, m), 1.63–1.2 (24H, m), 1.17 (3H, d, J=7 Hz), 0.89 (3H, d, J=7 Hz), 0.87 (3H, d J=7 Hz)

FABMS (m/z): 1511 (M+H)$^+$

IR (KBr): 3295, 2935, 1665, 1515, 1455, 1235, 1070 cm$^{-1}$ $[α]_D^{22}$=+17.1° (C=1.0, MeOH)

---

We claim:

1. A compound of the formula:

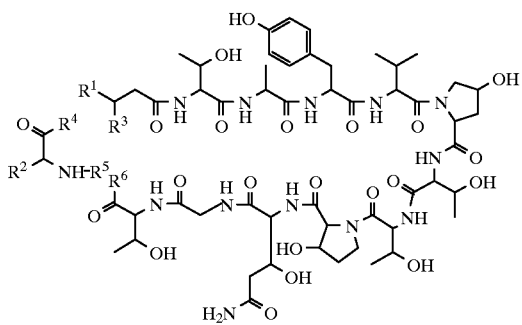

wherein $R^1$ is alkyl or aralkyl, $R^2$ is amino(lower)alkyl or protected amino(lower)alkyl, $R^3$ is hydroxy, protected hydroxy, amino or protected amino, $R^4$ is hydroxy, or $R^3$ and $R^4$ are linked together to form —Z— (in which —Z— is —O— or —NH—), and $R^5$ is hydrogen or an amino protective group, $R^6$ is hydroxy, or $R^5$ and $R^6$ are linked together to form bond, with proviso that when $R^3$ is hydroxy, protected hydroxy, amino or protected amino and $R^4$ is hydroxy, then $R^5$ and $R^6$ are linked together to form bond, or a pharmaceutically acceptable salt thereof.

2. A compound of claim 1, wherein $R^1$ is alkyl or phenylalkyl, $R^2$ is amino(lower)alkyl or acylamino(lower)alkyl, $R^3$ is hydroxy, acyloxy, amino or acylamino, $R^4$ is hydroxy, or $R^3$ and $R^4$ are linked together to form —Z— (in which —Z— is —O— or —NH—), and $R^5$ is hydrogen or acyl, $R^6$ is hydroxy, or $R^5$ and $R^6$ are linked together to form bond, with proviso that when $R^3$ is hydroxy, acyloxy, amino or acylamino, and $R^4$ is hydroxy, then $R^5$ and $R^6$ are linked together to form bond.

3. A compound of claim 2, wherein $R^1$ is $C_1$–$C_{13}$ alkyl or phenyl($C_1$–$C_6$)alkyl, $R^2$ is amino(lower)alkyl or lower alkoxycarbonylamino(lower)alkyl, $R^3$ is hydroxy, acyloxy, amino or ar(lower)alkoxycarbonylamino, $R^4$ is hydroxy, or $R^3$ and $R^4$ are linked together to form —Z— (in which —Z— is —O— or —NH—), and $R^5$ is hydrogen or ar(lower)alkoxycarbonyl, $R^6$ is hydroxy, or $R^5$ and $R^6$ are linked together to form bond, with proviso that when $R^3$ is hydroxy, acyloxy, amino or ar(lower)alkoxycarbonyl, and $R^4$ is hydroxy, then $R^5$ and $R^6$ are linked together to form bond.

4. A compound of claim 3, wherein $R^1$ is $C_1$–$C_{13}$ alkyl or phenyl($C_1$–$C_6$)alkyl, $R^2$ is amino(lower)alkyl or lower alkoxycarbonylamino(lower)alkyl, $R^3$ is hydroxy, acyloxy, amino or phenyl(lower)alkoxycarbonylamino, $R^4$ is hydroxy, or $R^3$ and $R^4$ are linked together to form —Z— (in which —Z— is —O— or —NH—), and $R^5$ is hydrogen or phenyl(lower)alkoxycarbonyl, $R^6$ is hydroxy, or $R^5$ and $R^6$ are linked together to form bond, with proviso that when $R^3$ is hydroxy, acyloxy, amino or phenyl(lower)alkoxycarbonyl, and $R^4$ is hydroxy, then $R^5$ and $R^6$ are linked together to form bond.

5. A process for preparing a compound of the formula:

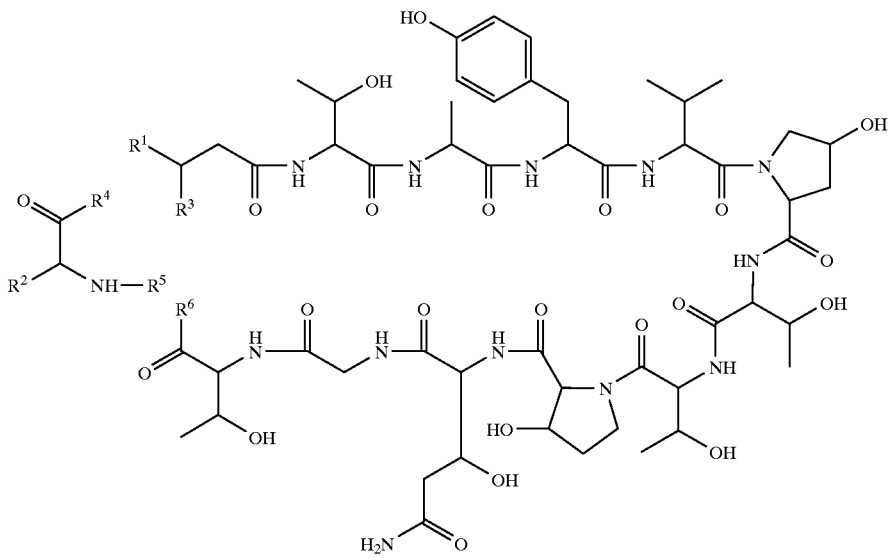

wherein
R¹ is alkyl or aralkyl,
R² is amino(lower)alkyl or protected amino(lower)alkyl,
R³ is hydroxy, protected hydroxy, amino or protected amino,
R⁴ is hydroxy, or
R³ and R⁴ are linked together to form —Z— (in which —Z— is —O— or —NH—), and
R⁵ is hydrogen or an amino protective group,
R⁶ is hydroxy, or R⁵ and R⁶ are linked together to form bond,
with proviso that
when
R³ is hydroxy, protected hydroxy, amino or protected amino and
R⁴ is hydroxy,
then R⁵ and R⁶ are linked together to form bond,
or a salt thereof,
which comprises
(1) reacting a compound of the formula:

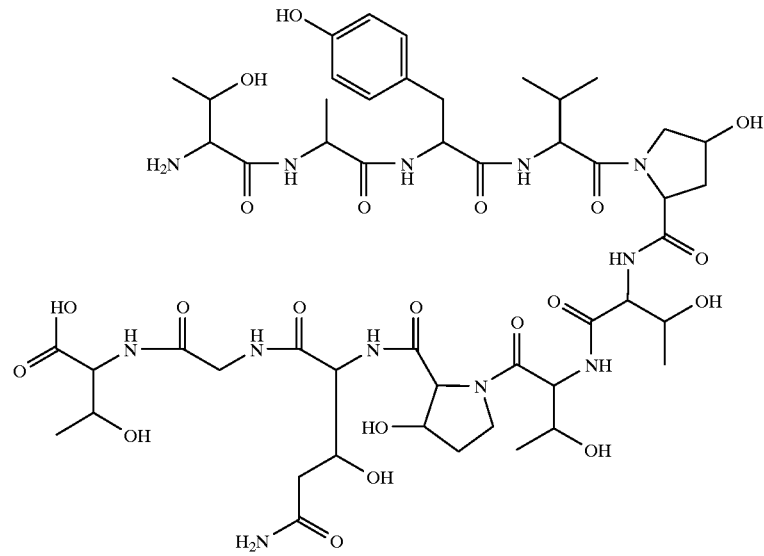

or its reactive derivative at the amino group, or a salt thereof with a compound of the formula:

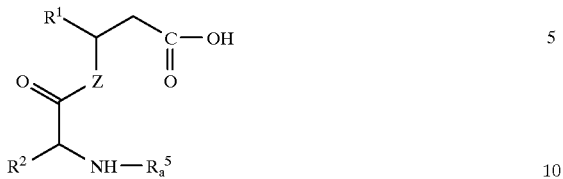

wherein
R¹, R² and Z are each as defined above, and
$R_a^5$ is hydrogen or an amino protective group,
or its reactive derivative at the carboxy group,
or a salt thereof to give a compound of the formula:

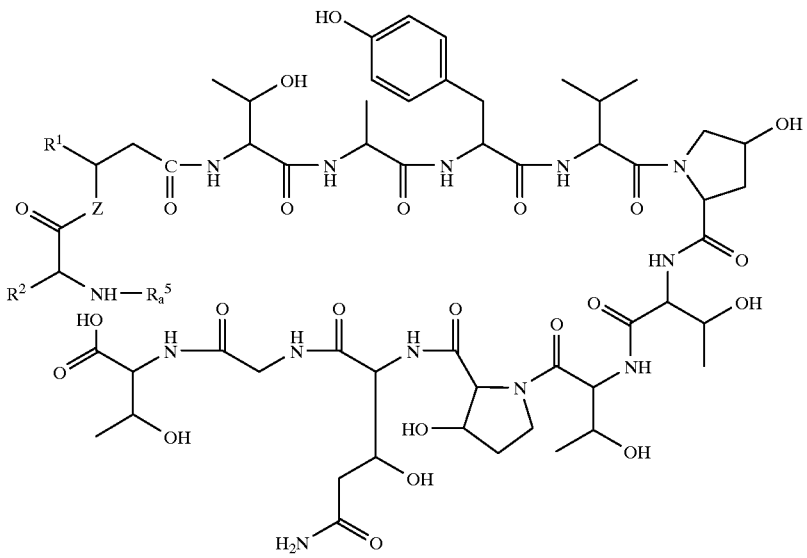

wherein $R^1$, $R^2$, $R_a^5$ and Z are each as defined above, or a salt thereof, or (2) subjecting a compound of the formula:

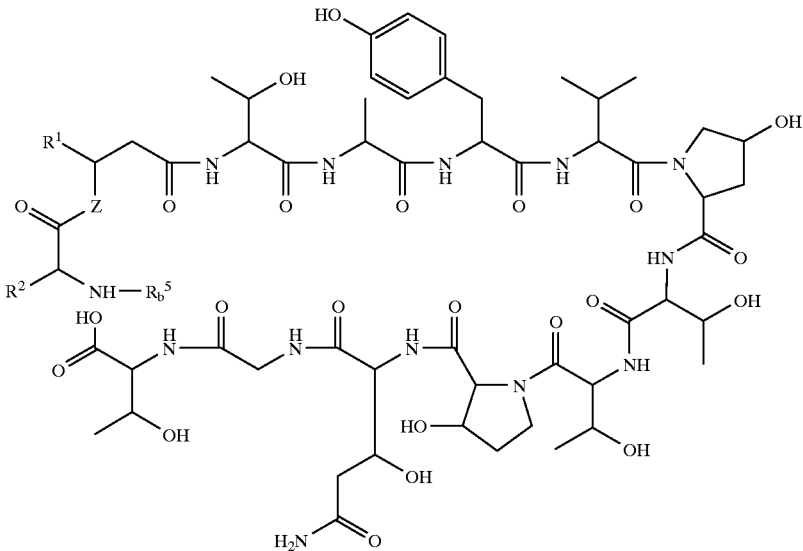
wherein
R¹, R² and Z are each as defined above, and
$R_b^5$ is an amino protective group,
or a salt thereof to elimination reaction of the amino protective group to give a compound of the formula:
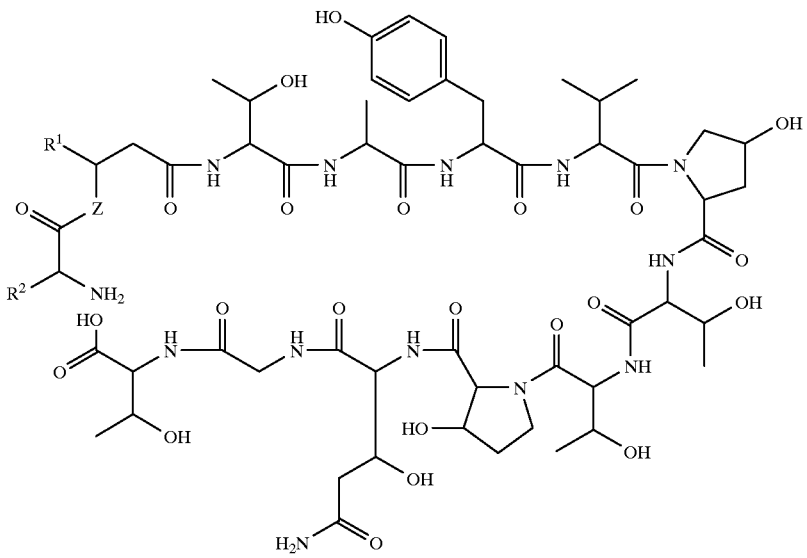
wherein R¹, R² and Z are each as defined above,
or a salt thereof,
or
(3) subjecting a compound of the formula:

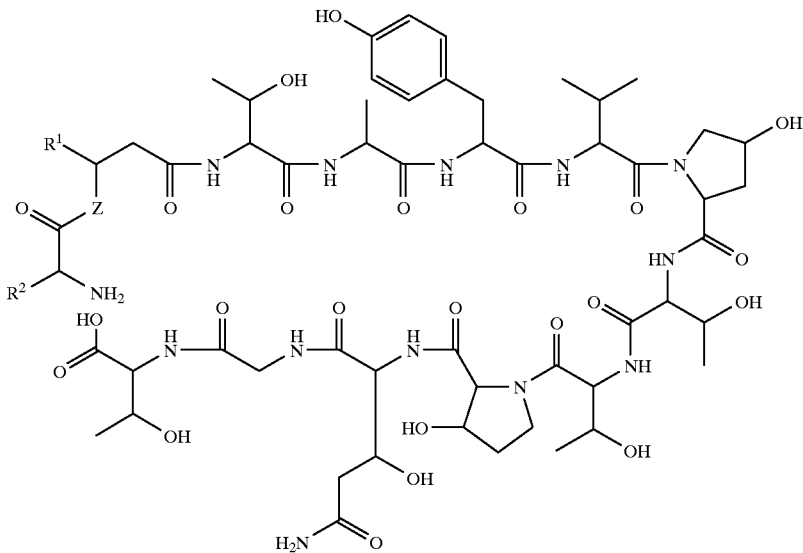
wherein $R^1$, $R^2$ and Z are each as defined above, or a salt thereof to cyclization reaction to give a compound of the formula:
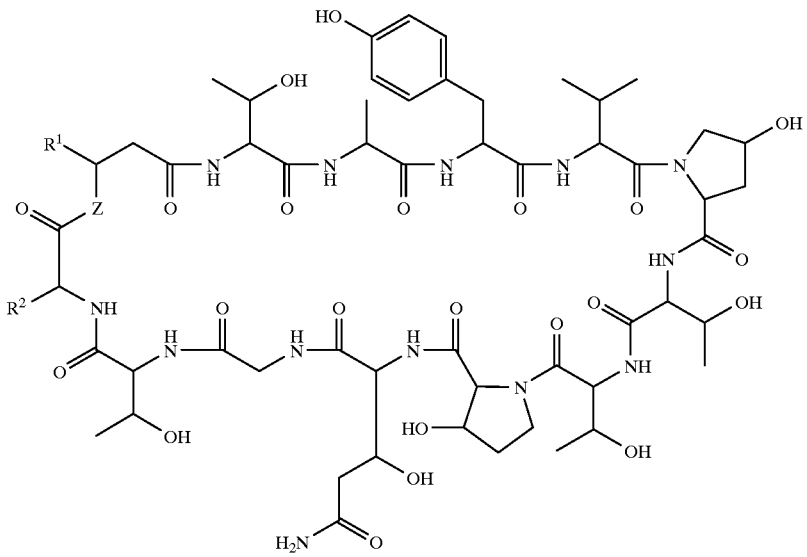
wherein $R^1$, $R^2$ and Z are each as defined above,
or a salt thereof,
or
(4) reacting a compound of the formula:

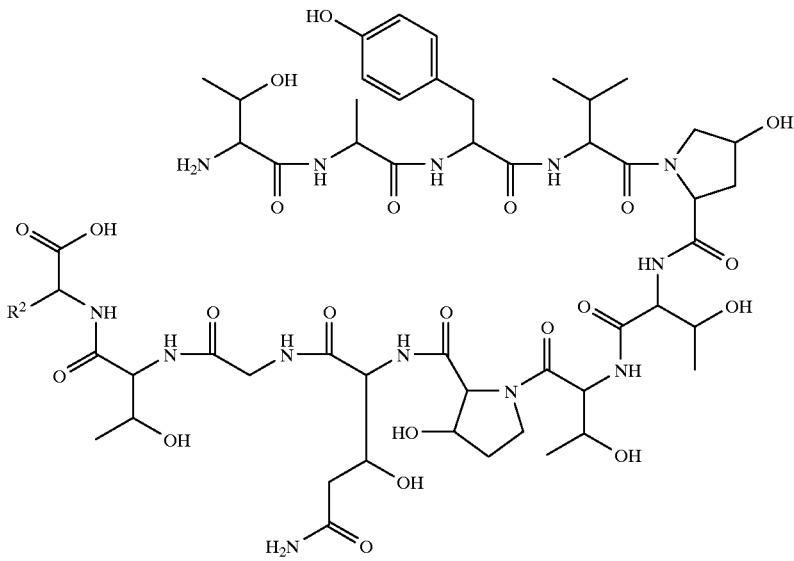

wherein R² is as defined above,
or its reactive derivative at the amino group, or a salt thereof with a compound of the formula:

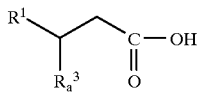

wherein

R¹ is as defined above, and $R_a^3$ is amino or protected amino, or its reactive derivative at the carboxy group, or a salt thereof to give a compound of the formula:

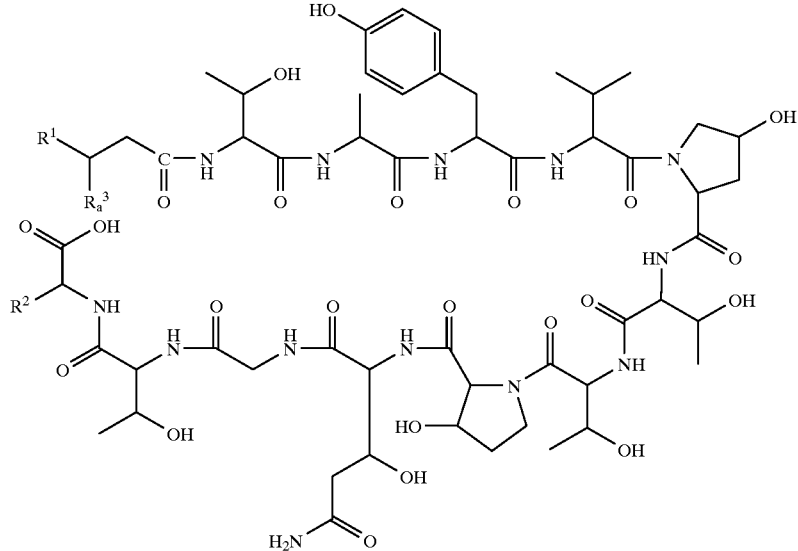

wherein R¹, R² and $R_a^3$ are each as defined above,
or a salt thereof,
or
(5) subjecting a compound of the formula:

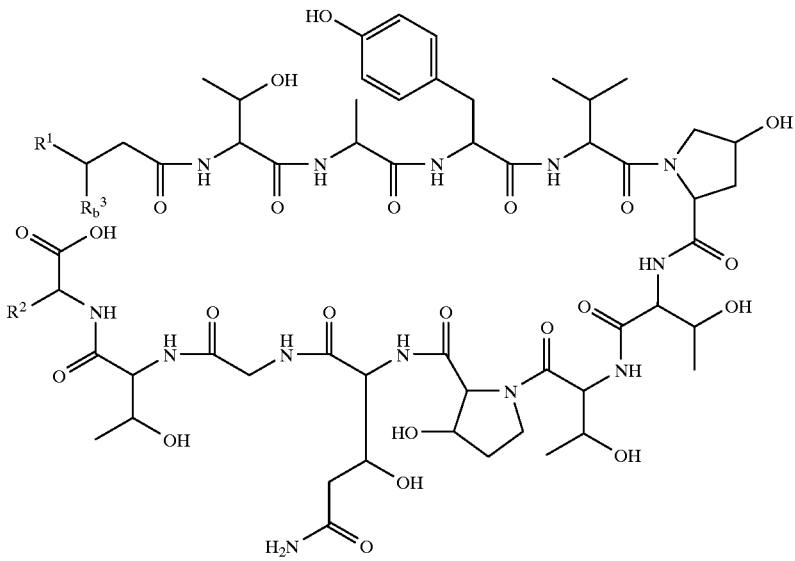
wherein
R¹ and R² are each as defined above, and
$R_b^3$ is protected amino,
or a salt thereof to elimination reaction of the amino protective group to give a compound of the formula:
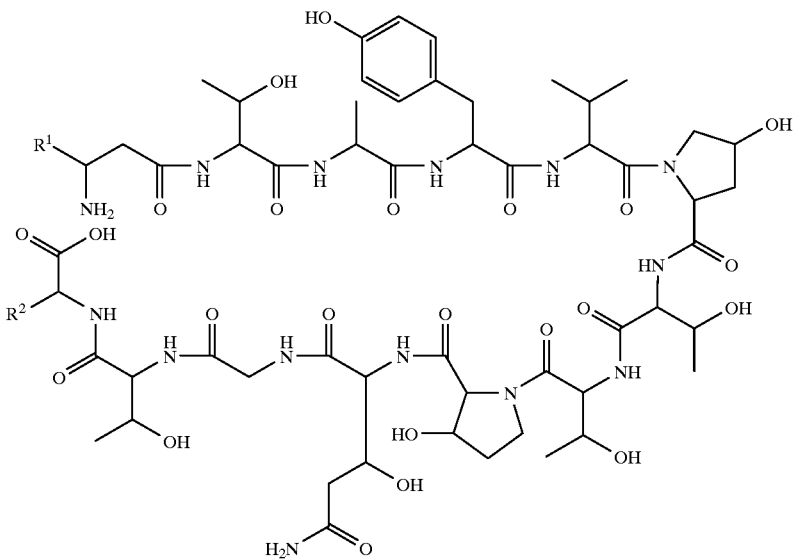
wherein R¹ and R² are each as defined above, or a salt thereof,
or
(6) subjecting a compound of the formula:

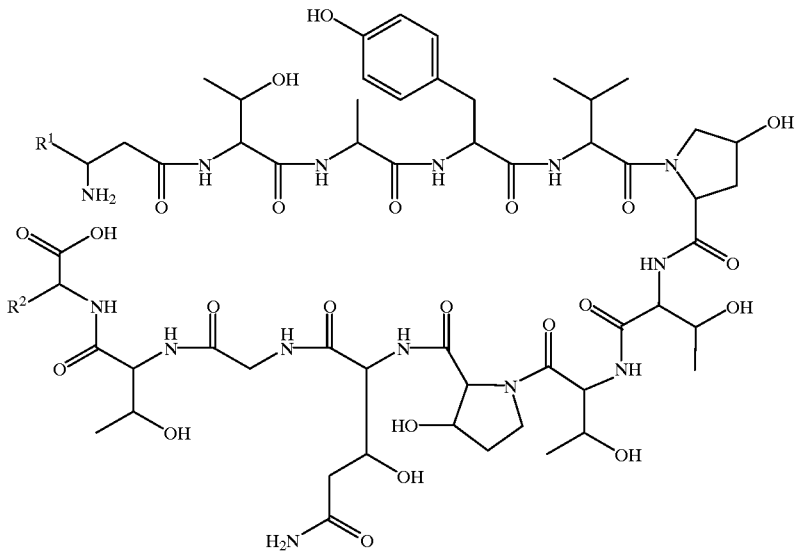
wherein R[1] and R[2] are each as defined above, or a salt thereof to cyclization reaction to give a compound of the formula:
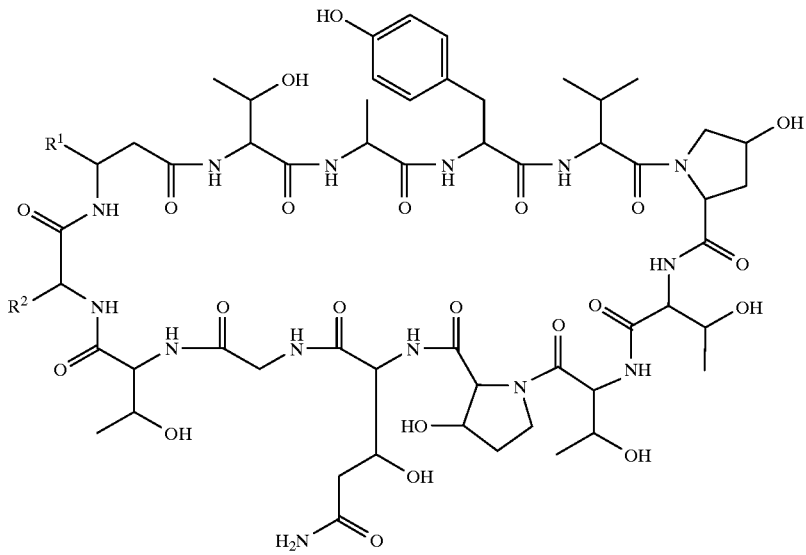
wherein R[1] and R[2] are each as defined above, or a salt thereof, or
(7) subjecting a compound of the formula:

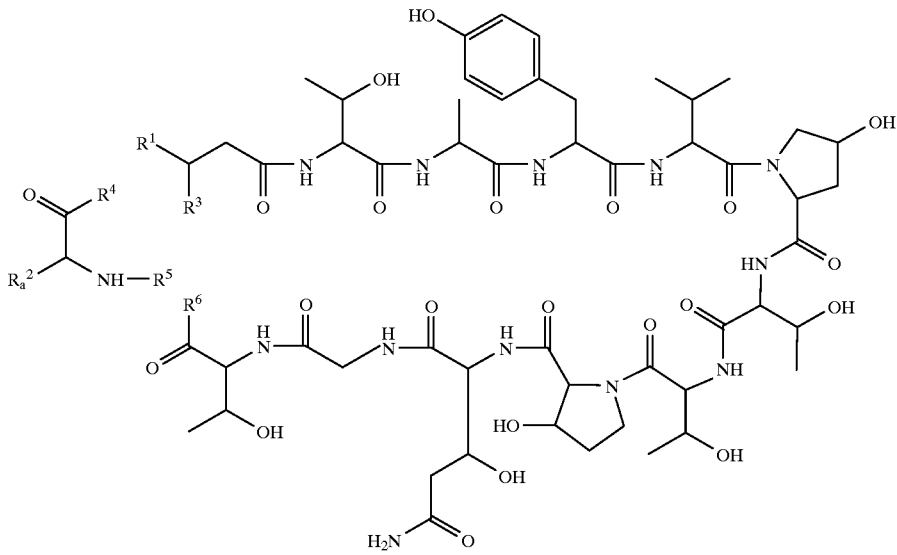
wherein
R¹, R³, R⁴, R⁵ and R⁶ are each as defined above, and
$R_a^2$ is amino(lower)alkyl,
or its reactive derivative at the amino group,
or a salt thereof to acylation reaction to give a compound of the formula:
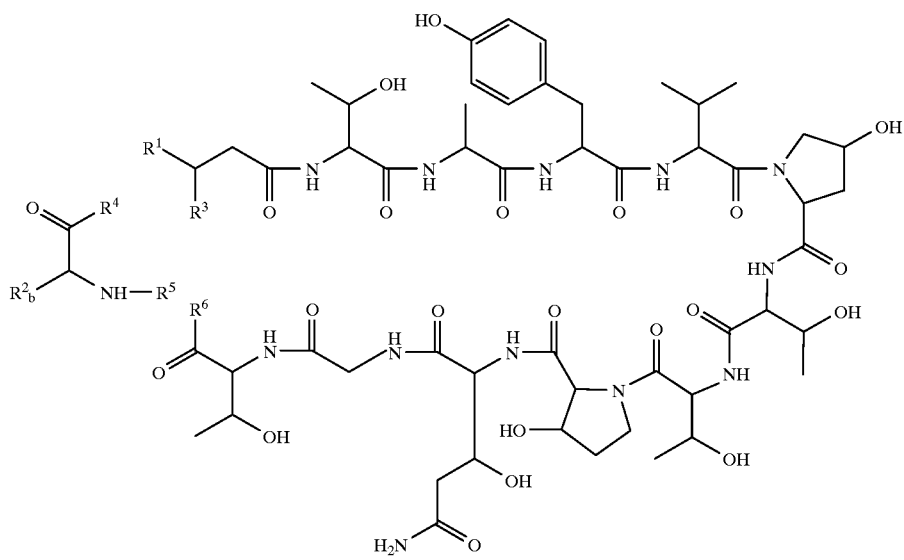
wherein
R¹, R³, R⁴, R⁵ and R⁶ are each as defined above, and
$R_b^2$ is acylamino(lower)alkyl,
or a salt thereof,
or
(8) subjecting a compound of the formula:

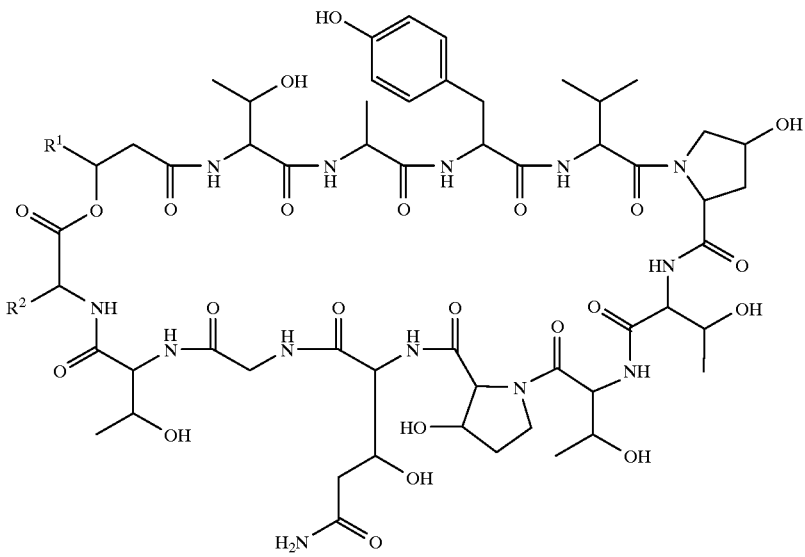
wherein $R^1$ and $R^2$ are each as defined above, or a salt thereof to hydrolysis reaction to give a compound of the formula:
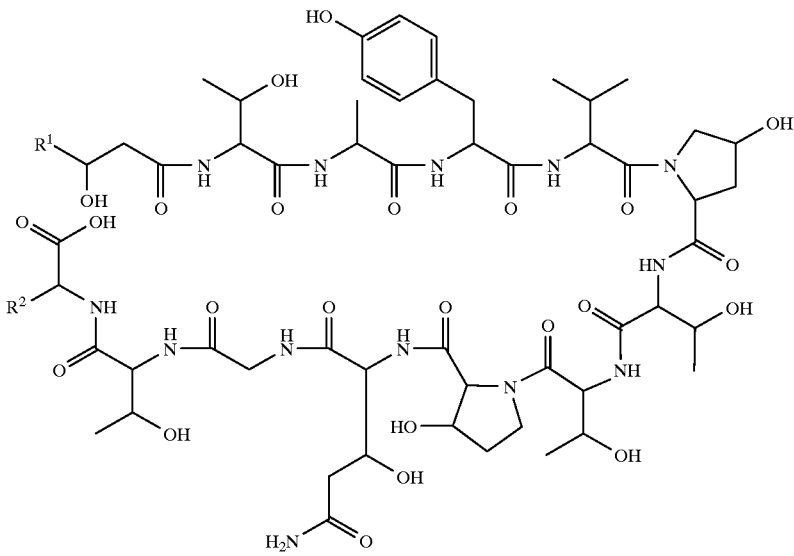
wherein $R^1$ and $R^2$ are each as defined above, or a salt thereof.
6. A compound of the formula:

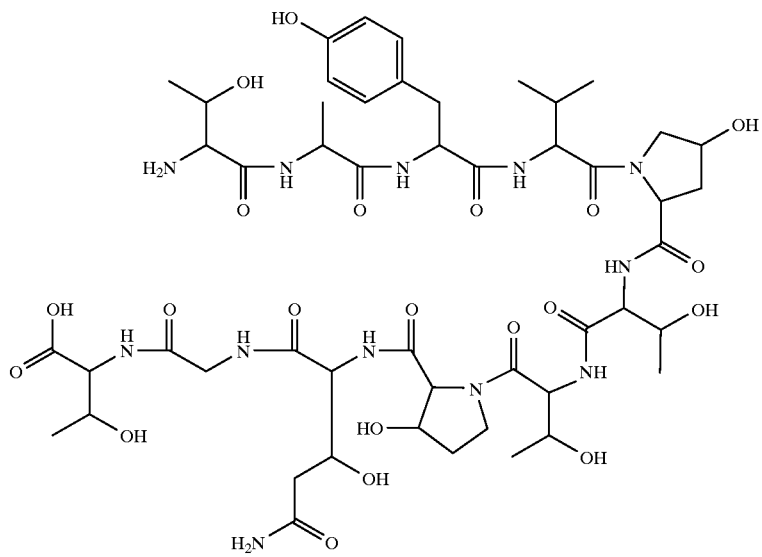
or a salt thereof.
7. A process for preparing a compound of the formula:
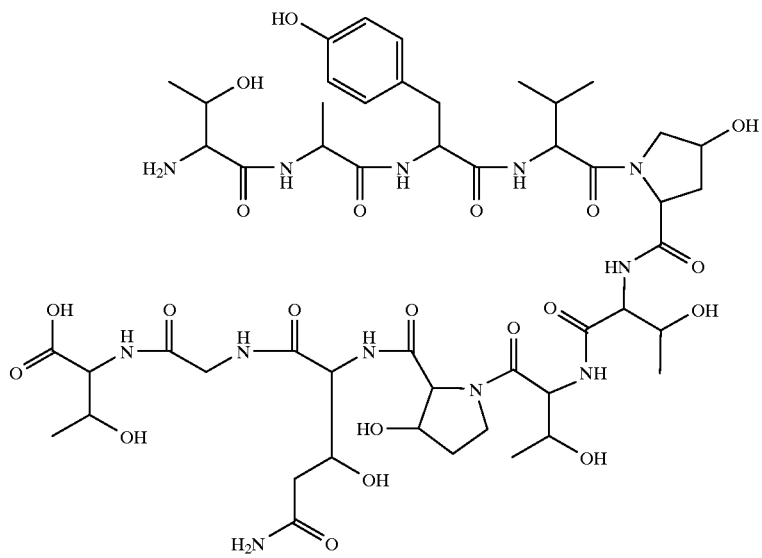
or a salt thereof,
which comprises subjecting a compound of the formula:

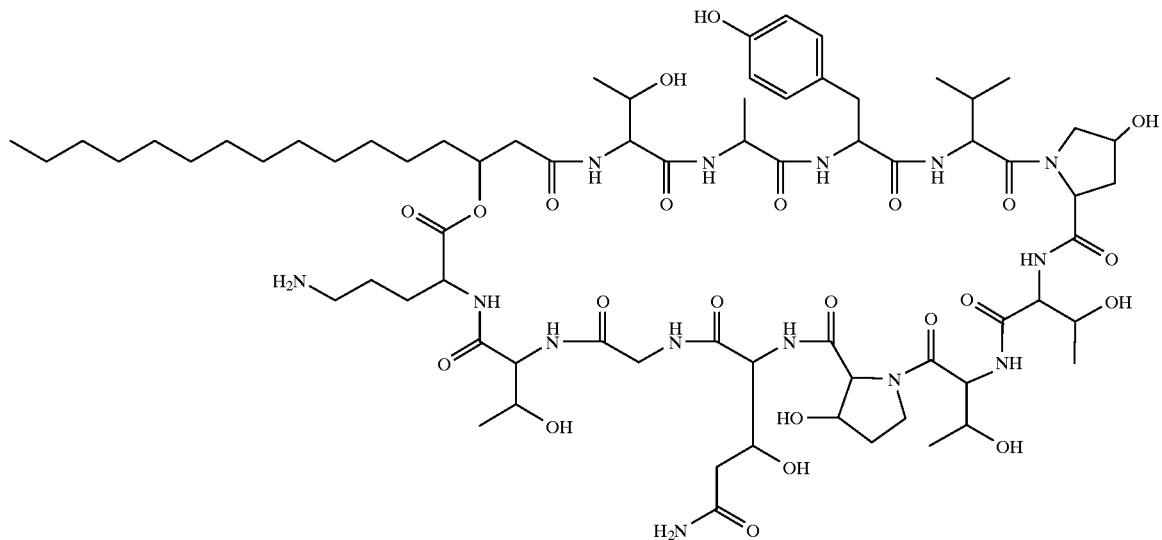
or a salt thereof to cleavage reaction of two amido bond by the enzyme.
8. A compound of the formula:
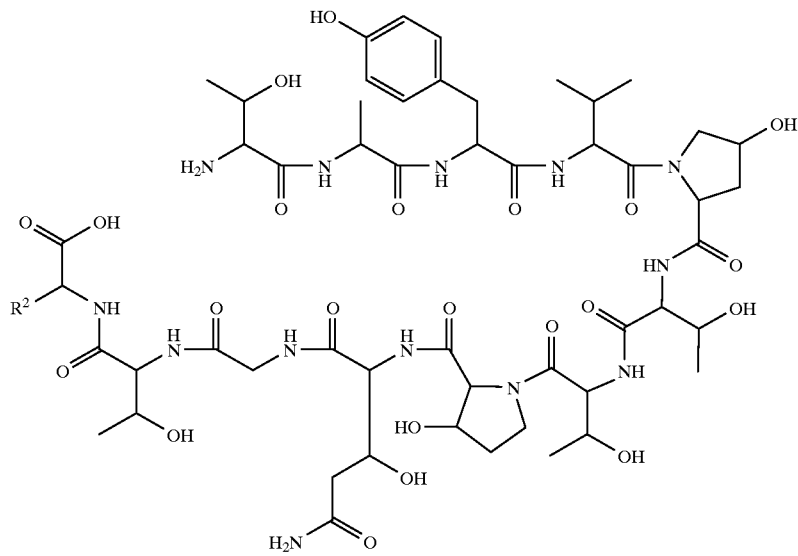
wherein $R^2$ is amino(lower)alkyl or protected amino(lower)alkyl,
or a salt thereof.
9. A process for preparing a compound of the formula:

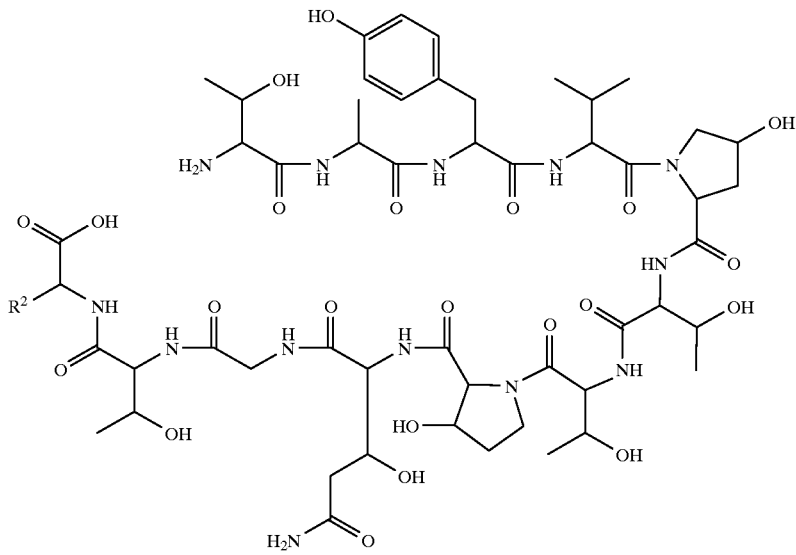

wherein R² is amino(lower)alkyl or protected amino(lower)alkyl,
or a salt thereof,
which comprises subjecting a compound of the formula:

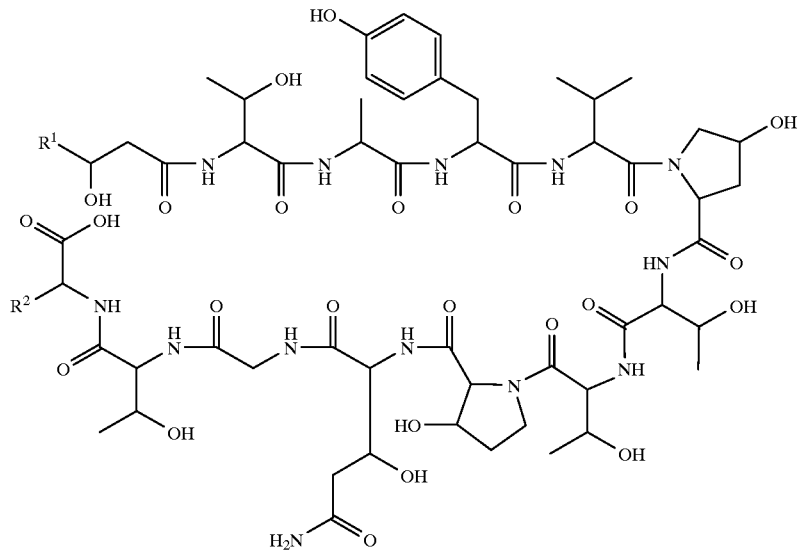

wherein
R² is as defined above, and
R¹ is alkyl or aralkyl,
or a salt thereof to deacylation reaction.

10. A pharmaceutical composition which comprises, as an active ingredient, a compound of claim 1 or a pharmaceutically acceptable salt thereof in admixture with pharmaceutically acceptable carriers or excipients.

11. A method for the prophylactic and/or the therapeutic treatment of infectious diseases caused by pathogenic microorganisms which comprises administering a compound of claim 1 or a pharmaceutically acceptable salt thereof to a human being or an animal.

* * * * *